(12) United States Patent
Takai et al.

(10) Patent No.: US 6,284,362 B1
(45) Date of Patent: Sep. 4, 2001

(54) ABSORBENT COMPOSITIONS, METHODS FOR PRODUCING THEREOF AND ABSORBENT PRODUCTS

(75) Inventors: Hitoshi Takai; Tsuyoshi Yuki; Shingo Mukaida; Daisuke Tagawa; Kenji Tanaka; Keiji Tanaka; Satoshi Tamabuchi; Yoshiyuki Iwasaki, all of Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 0 days.

(21) Appl. No.: 09/484,457

(22) Filed: Jan. 18, 2000

(30) Foreign Application Priority Data

| Jul. 18, 1997 | (JP) | 9-209848 |
| Aug. 7, 1997 | (JP) | 9-227429 |
| Nov. 18, 1997 | (JP) | 9-335074 |

(51) Int. Cl.$^7$ .............. B32B 5/16; B29B 1/04; B01G 20/28
(52) U.S. Cl. .......... 428/326; 428/903; 428/913; 442/398; 442/346; 604/358; 427/213
(58) Field of Search .............. 442/398, 346; 428/326, 903, 913; 608/358; 427/213

(56) References Cited

U.S. PATENT DOCUMENTS 5,436,066   7/1995   Chen ..................... 428/288
5,489,469   2/1996   Kobayashi et al. ............. 428/283

FOREIGN PATENT DOCUMENTS

| 89839 | 7/1981 | (JP) . |
| 10334 | 1/1982 | (JP) . |
| 501107 | 7/1983 | (JP) . |
| 18712 | 1/1984 | (JP) . |
| 86657 | 5/1984 | (JP) . |
| 185447 | 8/1988 | (JP) . |
| 251437 | 10/1988 | (JP) . |
| 267435 | 11/1988 | (JP) . |
| 30336 | 7/1990 | (JP) . |
| 25543 | 2/1994 | (JP) . |
| 216706 | 8/1995 | (JP) . |
| 310021 | 11/1995 | (JP) . |
| 10616 | 1/1996 | (JP) . |
| 289903 | 11/1996 | (JP) . |
| 9617884 | 6/1996 | (WO) . |

*Primary Examiner*—Richard Weisberger
(74) *Attorney, Agent, or Firm*—Shinjyu Global IP Counselors, LLP

(57) ABSTRACT

An absorbent composition is produced by drying a mixture obtained by mixing a micro-filler (B) with a hydrogel having a water absorptive resin (A) and water. The hydrogel is produced by performing polymerization to produce the resin (A) and not drying the resin (A) after the polymerization. The absorbent composition has a specific surface area at least 10% lager than that of a reference composition produced by drying the hydrogel without the micro-filler (B).

28 Claims, 1 Drawing Sheet

ABSORBENT COMPOSITIONS, METHODS FOR PRODUCING THEREOF AND ABSORBENT PRODUCTS

BACKGROUND OF THE INVENTION

1. Field of the Invention

This invention relates to absorbent compositions, methods for producing the absorbent compositions and absorbent products. More specifically, the present invention relates to water absorbents having a structure in which a water absorptive resin contains a built-in micro-filler so as to improve the surface area, absorption speed (especially diffusive absorption speed) and the initial amount of absorption under applied pressure. The present invention also relates to processes for manufacturing these absorbents and absorbent products using the water absorbents.

2. Background Information

Absorption speed of a water absorptive resin depends upon the surface area of the resin. That is, in a particle type water absorptive resin having a constant mass, the absorption speed of the resin becomes slower as the particle size becomes greater because the area that contacts the water becomes smaller. Conversely, the absorption speed becomes faster as the particle size becomes smaller because the contact surface area increases accordingly. However, if the particle size is too small, a phenomenon happens in which particles of the water absorptive resin cohere with each other via water (a phenomenon called "undissolved lumping") upon contact with water. Thus, the apparent absorption speed becomes slower.

In order to improve the absorption speed of a water absorptive resin, methods such as those described in ① to ⑥ below have been proposed:

① Adding surface active agents or a water soluble polymer on the surface of a small particle type water absorptive resin to prevent "undissolved lumping" (Japanese Patent Application Public Disclosure No. 2-30333);

② Producing a porous resin by adding a low boiling point volatile solvent to a polymerization solution to be used in the manufacturing process of a water absorptive resin, and vaporizing the volatile solvent by polymerization heat to obtain the porous resin (Japanese Laid-Open Patent Application No. 59-18712);

③ Producing a foam type resin by adding a crosslinking agent and a pyrolytic foaming agent to a mixture of a water absorptive resin having carboxyl groups and a polyolefin resin having glycidyl groups so as to generate foam by heat to obtain the foam type resin (Japanese Laid-Open Patent Application No. 63-251437);

④ Producing a porous water absorptive resin by dispersing a foaming agent comprising an azo compound having amino groups in an aqueous monomer solution containing an unsaturated monomer and a crosslinking agent so as to polymerize the monomer with the azo compound to obtain the porous water absorptive resin (Japanese PCT Laid-Open Publication No. WO 96-17884);

⑤ Granulating particles using water or a heat melting resin binder; and

⑥ Covering the surface of a water absorptive resin particle using porous inorganic particles, the covered particles weighing approximately some multiple of ten percent in relation to the total water absorptive resin particles.

However, the above-indicated methods are not completely satisfactory in terms of production and quality for the following reasons.

The water absorptive resin obtained by using a method based on ① has a problem when it is applied to a disposable diaper as an absorbent that is mixed with fibrous material such as pulp. The small resin particles tend to separate from the fibrous material.

Also, the water absorptive resin obtained by a method based on ① can generate problems such as a decrease in the ability of fine particles to flow because the particles are treated with a surface active agent or water soluble polymer. Deterioration of the operation environment can also occur because the fine particles can become the cause of dust generation.

According to the methods based on ② for making porous resin, while some improvement in the absorption speed is observed, a special explosion proof facility is required because a low boiling point volatile solvent is used.

According to the methods based on ③ in which a pyrolytic foaming agent is used, it is difficult to obtain a constant absorption speed and absorption performance. The difficulties arise because the material used, i.e., a water absorptive resin and a polyolefin resin, has no flexibility and discharges gases once the gas pressure reaches a certain level producing a large diameter non-uniform foam.

According to the methods based on ④ for producing porous resin, problems such as a decline in absorption performance are caused. This decline is due to a decrease in the molecular weight of the water absorptive resin and an increase in the amount of water soluble components. The decrease in molecular weight happens because a radical is concurrently produced when the azo compound, which has amino groups, decomposes and generates nitrogen gas.

According to the methods based on ⑤ in which particles are granulated using a binder, the improvement in absorption speed becomes insufficient when the adhesion force of the binder is increased. On the contrary, if the adhesion force of the binder is decreased, the mechanical strength of the granules are weaken and can be destroyed and return to powder by way of a screw feeder or mechanical shear during a powder transfer process.

The methods based on ⑥ in which the surface of a part of the water absorptive resin is covered by porous inorganic particles also have problems. For the methods based on ⑥, instant absorption speed at an initial absorption stage is somewhat improved due to an increase in the apparent surface area of the resin particle. However, no improvement is observed in terms of diffusive absorption speed inside the particle or an initial absorption amount under applied pressure. This is because no effect is obtained on the permeation of liquid inside the resin. Moreover, problems such as a lowering in absorption efficiency of a resulting composition are caused since the method requires using a large amount of inorganic particles.

The above mentioned methods ② to ⑥ are means to improve instant absorbability at an initial stage of absorption by increasing the surface area of resin particles. The methods have little effect on solving gel blocking. In other words, the above-mentioned "undissolved lumping" occurs when a large volume of water absorptive resin particles is present. Also, these methods have little effect on improving the diffusive absorption speed or the initial amount of absorption under applied pressure since the permeation of liquid to be absorbed inside the resin particle is not fully improved.

Also, when blood is the liquid to be absorbed, the above mentioned methods ① to ⑤ do not give completely satisfactory results. This lack of satisfactory results is because the viscosity of blood is relatively high and contains high molecular organic components such as blood corpuscles, hemoglobin, cytoplasm and proteins. Accordingly, a water absorptive resin that provides the desired blood absorption efficiency, both the desired amount of retention and the absorption speed, and is suitable for blood absorbent products such as menstrual products have been long awaited. In order to improve absorption performance of a water absorptive resin for blood, methods such as following ⑦ to ⑨ have been proposed:

⑦ Adding a salt of inorganic acids or organic acids to a water absorptive resin (Japanese Laid-Open Patent Application No. 58-501107);

⑧ Using a potassium salt or a lithium salt as a part of neutralizing salts for a water absorptive resin (Japanese Laid-Open Patent Application No. 6-25543);

⑨ Adding a polyamino acid (or salt) aqueous solution to a water absorptive resin, or polymerizing water soluble unsaturated monomer in the presence of a polyamino acid (or salt) and a cross link agent (Japanese Laid-Open Patent Application No. 7-310021).

According to the methods based on ⑦, some improvement in the blood absorption speed can be observed. The disadvantages are that the absorption efficiency and the amount of retention are lowered since a large amount of inorganic salt or organic salt must be used.

According to the methods based on ⑧, although the absorption efficiency for blood is improved to some extent, the level of the blood absorption speed is not satisfactory.

According to the methods based on ⑨, although the absorption performance for physiological saline is good, the absorption amount for blood is low, a mere 6 to 11 times the weight of the absorbent. Furthermore, the absorption speed level is unsatisfactory.

In view of the above, there exists a need for absorbent compositions, methods for producing them and absorbent products which overcome the above mentioned problems in the prior art. This invention addresses this need in the prior art as well as other needs, which will become apparent to those skilled in the art from this disclosure.

SUMMARY OF THE INVENTION

The inventors of the present invention, in view of the aforementioned prior art and after earnest studies, have created the present invention. A micro-filler is mixed with a water absorptive resin in a hydrogel prior to a drying step of the water absorptive resin in the hydrogel. The mixture is dried so that the water absorptive resin particles contain a built-in micro-filler.

The first purpose of the present invention is to provide an absorbent having a water absorptive resin with an improved surface area accompanied with an improved absorption speed. The absorbent has an improved instant absorption speed and an improved diffusive absorption speed inside the resin.

The second purpose of the present invention is to provide an absorbent in which problems associated with the above-mentioned methods ① to ⑥ are solved. The third purpose of the present invention is to provide absorbent products using the above-mentioned absorbents.

An absorbent composition according to the present invention is produced by a method including drying a mixture obtained by mixing a micro-filler (B) with a hydrogel having a water absorptive resin (A) and water. The hydrogel is produced by performing polymerization to produce the resin (A) and not drying the resin (A) after the polymerization.

The absorbent composition has a specific surface area at least 10% lager than that of a reference composition produced by drying the hydrogel without the micro-filler (B).

The absorbent composition may have an absorption speed (a time required for absorbing a certain amount) for physiological saline at least 20% less than that of the reference composition.

The absorbent composition may be a particle type absorbent having an average diameter that is in the range of 200 $\mu$m to 600 $\mu$m; and the absorbent may have particles of which diameters are between 150 $\mu$m and 500 $\mu$m; and specific surface areas may be at least 0.1 m$^2$/g by BET method.

The absorbent composition may have an absorption speed (a time required for absorbing a certain amount) for physiological saline at 25 seconds or less.

The absorbent composition may have a mass ratio of the water absorptive resin (A) and the micro-filler (B) in the range of 100:005 and 100:10.

The absorbent composition may be an apparent density of the micro-filler (B) that is 0.5 g/cm$^3$ or less.

The micro-filler (B) may have an apparent density of 0.1 g/cm$^3$ or less and an average particle size in the range of 1 $\mu$m to 200 $\mu$m.

The micro-filler (B) may have hollowed particles made of at least one selected from the group consisting of polyacrylate, polymethacrylate, polyvinylidene chloride, polyvinyl acetate and polyacrylonitrile.

The micro-filler (B) may be obtained by thermally expanding a thermal expansile hollowed filler having an average particle size in the range of 1 $\mu$m to 150 $\mu$m.

The micro filler (B) may be a hollowed resin filler containing a gas or a volatile substance inside thereof.

The micro-filler (B) may be a volume at least ten times as much as the thermal expansile hollowed filler.

The micro-filler (B) may have an apparent density which is more than 0.1 g/cm$^3$ and not more than 5 g/cm$^3$ and an average particle size in the range of 0.001 to 200 $\mu$m.

The micro-filler may be an inorganic filler.

The micro-filler may be made of one or a mixture of at least two selected from the group consisting of silicon oxide, aluminum oxide, iron oxide, titanium oxide, magnesium oxide, and zirconium oxide.

The method may further include adding a surface active agent (C) to the mixture after the drying.

The surface active agent (C) may be a nonionic surface active agent having an HLB of 8 to 14.

An absorbent composition includes surface crosslinking particles containing a built-in micro-filler (B) obtained by a method including: obtaining particles by drying and grinding a mixture obtained by mixing the micro-filler (B) with a hydrogel having a water absorptive resin (A) and water, the hydrogel produced by performing polymerization to produce the resin (A) and not drying the resin (A) after the polymerization; and surface-crosslinking the particles. The absorbent composition has a specific surface area at least 10% lager than that of a reference composition produced by drying the hydrogel without the micro-filler (B).

The mixture may contain the water 2 to 10 times as much as the water absorptive resin (A).

The resin (A) may have a crosslinked structure, and have an absorption amount for physiological saline under applied pressure of 20 g/cm$^2$ that is 25 g/g or more.

The absorbent may have a diffusive absorption speed for 0.9 mass % physiological saline in the range of 25 to 65 ml/g and an initial amount of absorption under applied pressure for 0.9 mass % physiological saline in the range of 18 to 40 g/g.

An absorbent composition produced by a method including adding a surface active agent (C) to a surface of adsorptive particles whose main composition is a water absorptive resin (A) having a bulk density in the range of 0.1 to 0.55 g/cm$^3$ and an average particle size in the range of 200 to 600 μm. The absorbent composition has an absorption speed for sheep blood that is 30 seconds or faster and a water retention amount after swelling in sheep blood for 30 minutes that is 20 g/g or more.

A method for producing an absorbent composition includes obtaining a mixture by mixing a micro-filler (B) having an apparent density of 5 g/cm$^3$ or less with a hydrogel having a water absorptive resin (A) and water, the hydrogel produced by performing polymerization to produce the resin (A) and not drying the resin (A) after the polymerization; and drying the mixture.

The micro-filler (B) may have an apparent density of 0.1 g/cm$^3$ or less and an average particle size in the range of 1 μm to 200 μm.

The micro-filler (B) may have an apparent density which is more than 0.1 g/cm$^3$ and not more than 5 g/cm$^3$ and an average particle size in the range of 0.001 μm to 200 μm.

The micro-filler (B) may be obtained by thermally expanding a thermal expansile hollowed filler having an average particle size in the range of 1 μm to 150 μm.

The method may further include surface-crosslinking the mixture after the drying.

The method may further include adding a surface active agent (C) onto the mixture after the drying.

An absorbent product includes an absorption layer having an absorbent composition and a fibrous material, the absorbent composition produced by a method comprising drying a mixture obtained by mixing a micro-filler (B) with a hydrogel having a water absorptive resin (A) and water; the hydrogel produced by performing polymerization to produce the resin (A) and not drying the resin (A) after the polymerization; the absorbent composition having a specific surface area at least 10% lager than that of a reference composition produced by drying the hydrogel without the micro-filler (B); and a surface protection sheet covering the absorption layer, and having a water permeable portion.

According to the above absorbent compositions and the manufacturing methods of the present invention, the following characteristics and effects can be achieved:

① The absorption speed under atmospheric pressure is fast and the initial amount of absorption under applied pressure (i.e., the absorption speed under applied pressure) is excellent. Thus, effects Such as an improvement in an initial feeling of dryness and a decrease in leaking can be realized when the compositions are applied to, for instance, absorbents for sanitary products;

② In addition to ①, each of the compositions has an excellent amount of retention and amount of absorption under applied pressure;

③ Since the effects set forth in the above ① and ② are realized even if the compositions are of a normal particle size, they are excellent in terms of particle handling. Also, according to the present invention, almost no fine particles are generated by mechanical shear or abrasion unlike the cases of conventional fine particles or granulates;

④ When used as an absorbent being mixed with fibrous material such as pulp, almost none of them are separated from the fibrous material even if an external force such as a vibration is applied. Thus, the effects set forth in the above ① and ② are realized even if the compositions are of a normal particle size;

⑤ Unlike an improvement of absorption speed obtained by using a pyrolytic foaming agent, an absorbent composition having an excellent absorption ability and a small amount of water soluble components can be obtained. This is because no radicals are generated during a heat-drying process;

⑥ The absorption speed can be improved by a simple method in which a micro-filler is added to hydrogel at any stage between prior to polymerization of water absorptive resin and prior to a drying step thereof;

⑦ The absorption speed of the compositions, which are treated with a surface active agent, with relation to handling blood and menstrual flow and the amount of retention is excellent. Effects such as an improvement in surface dryness and a decrease in leaking can be realized when they are applied, for instance, to absorbents for sanitary products (especially sanitary napkins). Also, excellent absorption performance and absorption speed can be realized for other bodily fluids (urine, breast milk, amniotic fluid when giving birth, etc.); and ⑧ By applying the compositions treated with a surface active agent to absorbent products such as sanitary napkins, products which have excellent absorption speed, diffusion area, surface dryness, amount of retention and so forth, when compared with products obtained by using conventional water absorptive resins, can be obtained.

Since the absorptive compositions according to the present invention have the above-mentioned effects, they are particularly suitable for various absorbent products. For example, sanitary products and medical products such as disposable diapers for babies and adults, sanitary napkins, pads for incontinence, pads for breast milk, under-pads for operation, mats for a delivery bed, dressing materials for protecting a cut, bed sheets and so forth are all suitable products. Also, they are suitable for use in various absorbent sheets (for instance, absorbent sheets for pet urine, wrapping sheets for maintaining freshness, drip absorption sheets, rice plant raising sheets, sheets used for concrete production, water-running protection sheets for cables and so forth). Moreover, the present invention can be suitably employed for use in which powder type absorbent compositions are applied (for instance, soil water retention agents, sludge solidifying agents, solidifying agents for damp blood or aqueous waste liquid, urine gelling agents, gelling agents for battery electrolytes and so forth).

These and other objects, features, aspects and advantages of the present invention will become apparent to those skilled in the art from the following detailed description, which, taken in conjunction with the annexed drawing, discloses preferred embodiments of the present invention.

BRIEF DESCRIPTION OF THE DRAWING

Referring now to the attached drawing which forms a part of this original disclosure.

DETAILED DESCRIPTION OF THE PREFERRED EMBODIMENTS

Examples of Water Absorptive Resins (A)

Figure 1:
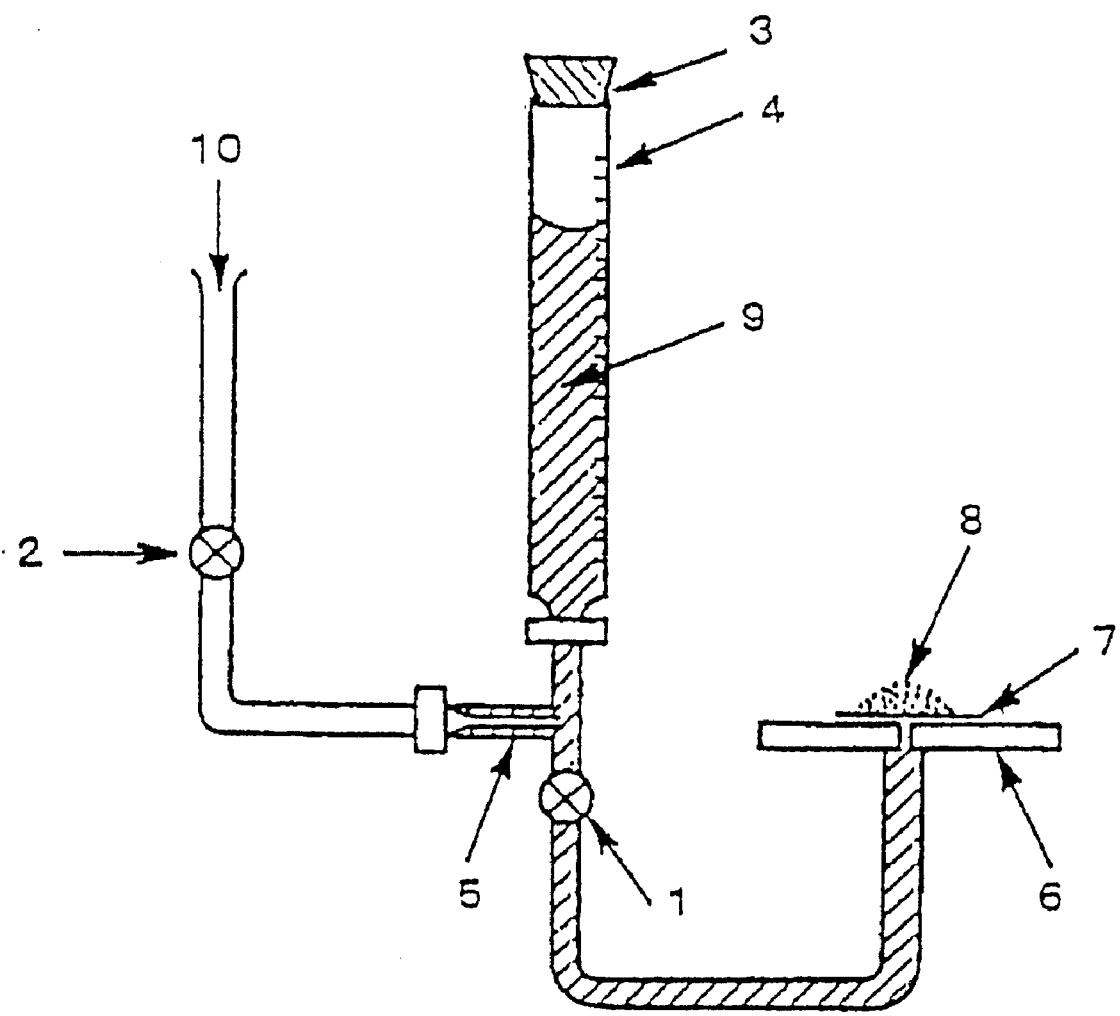
FIG. 1 is an elevational view of a device used for measuring a diffusive absorption speed of compositions.

Examples of water absorptive resins (A) used in water absorption compositions [1] and [2] according to the present invention include the following ① to ④:

① Water absorptive resins of water insoluble, water swelling polymer having a crosslinked and/or graft structure. The polymer can be obtained by polymerizing a radical polymerizable monomer (a) that is water soluble or becomes water soluble by hydrolysis with a polyfunctional compound (b). The polyfunctional compound (b) is preferably selected from a group made of crosslinking agents (b1) and grafting bases (b2), and subjecting to hydrolysis if necessary.

② Water absorptive resins having a water insoluble, water swelling structure obtained preferably by crosslinking the surface of a polysaccharide of a particle type. Examples include structures obtained by crosslinking the surface of water soluble polysaccharide particle such as gua gum, xanthan gum, cellulose, methylcellulose, ethylcellulose, carboxylmethylcellulose and denaturations thereof using a polyfunctional crosslinking agent.

③ Water insoluble, water swelling polymer obtained preferably by polymerizing a water soluble radical polymerizable monomer and subjecting it to self crosslinking (for example, self crosslinked polyacrylate).

④ Water insoluble, water swelling polymer obtained by polymerizing a water soluble radical polymerizable monomer and subjecting it to thermal crosslinking. For example, a water swelling polymer obtained by thermally crosslinking a copolymer of acrylamide and acrylic acid (acrylate) can be used.

In the water absorptive resin ①, examples of water soluble or solbilizable by hydrolysis radical polymerizable monomers (a1) of the monomer (a) include water soluble radical polymerizable monomers, salts of water soluble radical monomers, and nonionic water soluble radical polymerizable monomers (a13). The water soluble radical polymerizable monomers preferably have acid groups such as carboxlic acid, sulfonic acid or phosphoric acid (a11). The salts of water soluble radical monomers preferably have the aforementioned acid groups (a12).

Among (a11), examples of the water soluble radical polymerizable monomers having a carboxylic acid group include, for instance, unsaturated mono or polycarboxylic acids [e.g. (meth)acryl acid (this expression means acryl acid and/or methacryl acid, hereinafter the same definition is applied), crotonic acid, sorbic acid, maleic acid, itaconic acid, cinnamic acid, and salts thereof], and anhydride thereof [for instance, maleic anhydride].

Among (a11), examples of the water soluble radical polymerizable monomers having a sulfonic acid group include, for instance, aliphatic or aromatic vinylsulfonic acids (e.g. vinylsulfonic acid, acrylsulfonic acid, vinyltoluene sulfonic acid, and styrene sulfonic acid), (meth)acryl alkylsulfonic acid, [e.g. sulfoethyl (meth)acrylate, and sulfopropyl (meth)acrylate], (meth)acrylamidalkylsulfonic acid [e.g. 2-acrylamid-2-methylpropanesulfonic acid], and salts thereof.

Among (a11), examples of water soluble radical polyenrizable monomers having a phosphoric acid group include, for instance, hydroxyalkylphosporic acid monoester (meth)acrylate [e.g. (meth)acryloyloxy-2-hydroxyethylphosphate, and phenyl-2-acryloyloxyethylphospate].

Types of salts among (a12) include alkali metal salts, ammonium salts, amine salts and so forth, and the alkali metal salts, especially sodium salts and potassium salts are preferable.

Examples of the nonionic water soluble radical polymerizable monomers (a13) include (meth)acrylamide, and vinylpyrrolidone.

Among the monomers (a), examples of a radical polymerizable monomers capable of water soluble by hydrolysis (a2) include (meth)acrylonitrile, lower alkyl(meth)acrylate (the number of carbon atoms in alkyl group is 1 to 4), and lower alkylmaleate (the number of carbon atoms in alkyl group is 1 to 4).

As for the monomers (a) described above, it is possible to use two or more of them together.

Also, when the water absorptive resin (A) is a resin having an acid group and/or a salt thereof, the neutralization degree of the acid groups in the resin is preferably 50 to 90 mol %, especially preferably is 60 to 80 mol %. The neutralization can be carried out at a monomer stage prior to the polymerization. It is also possible to perform the neutralization after the polymerization.

Examples of the crosslinking agent (b1) include a crosslinking agent having two or more of ethylenic unsaturated groups (b11), a crosslinking agent having an ethylenic unsaturated group and a reactive functional group (b12), a crosslinking agent having two or more of reactive functional groups (b13) and so forth.

Examples of the crosslinking agent (b11) include N,N'-methylene bis-(meth)acrylamide, ethylene glycol di(meth)acrylate, polyethylene glycol di(meth)acrylate, propylene glycol di(meth)acrylate, glycol(di or tri)acrylate, trimethylolpropane triacrylate, triallylamine, triallylcyanurate, triallylisocyanurate, tetraallyloxyethane, pentaerythritol triallyether and so forth.

Examples of the crosslinking agent (b12) include glycidyl (meth)acrylate, N-methylol(meth)acryl amide and so forth.

Examples of the crosslinking agent (b13) include ethylene glycol, diethylene glycol, glycerol, propylene glycol, diethanol amine, trimethylol propane, polyethylene imine and so forth.

Two or more of the above-mentioned crosslinking agents can be used together. Among them the crosslinking agents (b11), inter alia N,N'-methylene bis-acrylamide, ethylene glycol diacrylate, trimethylolpropane triacrylate, tetraallyloxy ethane, pentaerythritol triallyether and triallylamine are preferable. Examples of the grafting base (b2) include water soluble polysaccharides such as starch, gua gum, xanthan gum, cellulose, methylcellulose, ethylcellulose, carboxylmethylcellulose, denaturation thereof, and polyvinyl alcohol.

In order to form the crosslink structure and/or graft structure, one or more polyfunctional compounds (b) are used for the water absorptive resin (A). The polyfunctional compound or compounds (b) are selected from the group preferably made of the crosslinking agents (b1) and the grafting bases (b2).

The amount of the crosslinking agent (b1) used for forming a crosslink structure is generally 0.001 to 5%, preferably 0.05 to 2%, and more preferably 0.1 to 1%. This amount is based on the total mass of the monomer (a) and the crosslinking agent (b1).

If the amount of the crosslinking agent (b1) is 0.001% or less, the resin becomes a sol when it absorbs water. The water absorbing/retention performance, which is a function of a water absorptive resin, decreases. Moreover, it is very slow to dry and the productivity becomes inefficient. On the other hand, if the amount of the crosslinking agent exceeds 5%, the degree of crosslinking becomes too much and cannot exert sufficient water absorbing/retaining function.

The amount of grafting base (b2) used for forming a graft structure does not generally exceed 30% by mass and is preferably 0.1 to 20% by mass, and more preferably 1 to 10% by mass. This amount is based on the total mass of the monomer, the crosslinking agent (b1) and the grafting base.

Examples of the water absorptive resin ① include saponificated starch-acrylonitrile copolymer, crosslinked starch-acryl ate copolymer, crosslinked polyacrylate, saponificated and crosslinked (meth)acrylate-vinylacetate copolymer, crosslinked isobutylene/maleic anhydride copolymer, crosslinked polysulfonate, crosslinked polyacrylate/polysulfonate copolymer, crosslinked polyacrylate/polyacrylamide copolymer, crosslinked polyacrylamide and hydrolyzed products thereof, crosslinked polyvinylpyrrolidone, crosslinked cellulose derivatives and so forth.

The main component or components of the water absorptive resin (A) are preferably polyenrizable monomers having a carboxylate group and/or a carboxyl group, which afford ability of absorbing/holding a large amount of liquid by ion osmotic pressure and discharges little water when a load or external force is applied. The water absorptive resin (A) is more preferably a crosslinked starch-acrylate copolymer and a crosslinked polyacrylate.

In case the above-mentioned water absorptive resin (A) is in a neutralization salt form, the preferred salts are alkali metal salts, inter alia sodium salts and potassium salts. The degree of neutralization for the acid groups is preferably 50 mol % to 90 mol %, and more preferably 60 mol % to 80 mol %.

In order to obtain a water absorptive resin ①, it is possible to add, if necessary, various additives, chain transfer agents (for instance, thiol compounds), surface active agents and so forth, to a polymerization system polymerizing the monomer (a) and the polyfunctional compound (b).

Methods for manufacturing the water absorptive resin (A) are not particularly limited and include an aqueous solution polymerization method, a reverse phase suspension polymerization method, a spray polymerization method, a radiation polymerization method and so forth. A preferred polymerization method is the aqueous solution polymerization method by using a starting agent of radical polymerization. In this case, the type of a radical starting agents and condition for the radical polymerization are not particularly limited and conventional ones can be used.

Examples of Micro-fillers (B)

The water absorptive compositions [1] and [2] according to the present invention have a structure in which the water absorptive resin (A) contains a built-in micro-filler (B).

The apparent density of a particle (hereinafter referred to as apparent density) of the micro-filler (B) is 5 g/cm³ or less. However, the effect of the micro-filler (B) is different if the apparent density is ① 0.1 g/cm³ or less, or ② more than 0.1 g/cm³ but 5 g/cm³ or less. The apparent density of a particle is a density measured by using PYCNOMETER and indicates a mass per unit volume including the pores of the particle.

The apparent density is practically measured as follows:

Two chambers, i.e., a cell chamber and an expansion chamber, which are connected by valves, are present in the PYCNOMETER. The volume of each chamber is expressed as V(c) and V(e), respectively. The mass (W) of a sample is measured in the cell chamber (the volume of the sample is expressed as V). The valve connecting to the expansion chamber is closed to obtain a constant pressure P(1) inside the cell chamber. The pressure inside the expansion chamber at that time is P(a). Then, the valve connecting to the expansion chamber is opened and the pressure P(2) of the both chambers is measured. The volume of the sample can be calculated from the volume and the pressure changes of the both chambers, and the apparent density is obtained using the following equation:

Apparent density=$W/V=W/[V(c)+V(e)\times\{P(a)-P(2)\}/\{P(1)-P(2)\}]$

① when the apparent density is 0.1 g/cm³ or less

The apparent density of (B) is generally about 0.1 g/cm³ or less, preferably 0.08 g/cm³ or less, and more preferably 0.01 g/cm³ to 0.06 g/cm³.

If the apparent density of (B) is 0.1 g/cm³ or less, the absorption speed of the resulting water absorbent is improved because the volume and surface area of the water absorbent are efficiently increased.

Examples of the micro-filler (B) include a micro-filler (B1) and a micro-filler (B2). The particle size of the micro-filler (B1) is between 1 μm and 200 μm. The micro-filler (B2) includes a thermally expanded thermally expansive hollowed filler (B2') having a particle size between 1 μm and 150 μm. The micro-filler (B1) and the micro-filler (B2), with an arbitrary ratio, can be contained in the water absorptive resin (A).

The particle size of (B1) is generally 1 μm to 200 μm, preferably 1 μm to 150 μm, and more preferably 5 μm to 100 μm. When the particle size of (B1) is 200 μm or less, the absorption speed of the resulting water absorbent is efficiently improved since the uniformity obtained when (B) is mixed with a hydrogel of (A) is excellent during a manufacturing process [4]. On the other hand, if the particle size is 1 μm or more, an excellent uniformity is obtained when (B1) is mixed with a hydrogel of (A) since the agglutination among (B1) is hardly generated.

The material of (B1) are not limited and can be an organic or inorganic material. Examples of the organic material include polyethylene, polypropylene, polystyrene, poly-p-xylylene, polyacrylate, polymethacrylate, poly(vinyl chloride), poly(vinylidene chloride), poly(vinyl acetate), fluorine-contained resin, polyacrylonitrile, poly(vinyl ether), polybutadiene, polyamide, thermal plastic polyester, polycarbonate, poly(phenylene oxide), polysulfone, thermal plastic polyurethane, poly(ethylene oxide), poly(propylene oxide), poly(tetramethylene oxide), polyacetal, cellulose derivatives and so forth. Ones which can be obtained by copolymerizing two or more monomers forming these resins are also included in the examples.

Examples of the possible inorganic material include silicon oxide, aluminum oxide, iron oxide, titanium oxide, magnesium oxide, zirconium oxide and so forth. Two or more of these can be used together. Among them, the organic materials are preferable and, inter alia, polyacrylate, polymethacrylate, poly(vinylidene chloride), poly(vinyl acetate) and polyacrylonitrile are more preferable.

The shape of (B1) is not particularly limited and can be hollowed, porous and so forth. The hollowed shape is preferable. Practical examples of the micro-filler (B1) include, for instance, Expansel 551DE, 461DE, and 091DE manufactured by Japan Ferrite Co. Two or more of these can be used together.

On the other hand, the micro-filler (B2) contained in the water absorptive resin (A), is a micro-filler that is formed when the thermal expansive hollowed filler (B2') of particle size 1 μm to 150 μm is thermally expanded. An example of the thermal expansive hollowed fillers (B2') is, for instance, hollowed fine resin having a gas or volatile compound inside.

Examples of the kind of resin which forms the outer surface of the hollowed fine resin include, for instance, polyethylene, polypropylene, polystyrene, poly-p-xylyene, polyacrylate, polymethacrylate, poly(vinyl chloride), poly (vinylidene chloride), poly(vinyl acetate), fluorine-contained resin, polyacrylonitrile, poly(vinyl ether), polybutadiene, polyamide, thermal plastic polyester, polycarbonate, poly(phenylene oxide), polysulfone, thermal plastic polyurethane, poly(ethylene oxide), poly(propylene oxide), poly(tetramethylene glycol), polyacetal and so forth. Ones which can be obtained by polymerizing two or more of monomers forming these resins are also included in the examples. Two or more of the above examples can be used in combination. Among these resins, polyacrylate, poly(vinylidene chloride), and polyacrylonitrile are preferable.

The temperature at which (B2') starts to expand can be varied according to the softening temperature of the resin, types of gases present inside, or the kind of the volatile compound. However, the temperature at which (B2') starts to expand is preferably between 60° C. and 150° C. On the other hand, the maximum expansion temperature is preferably between 80° C. and 180° C. It is more preferable that the temperature at which expansion starts to be between 70° C. and 120° C. and the maximum expansion temperature to be between 90° C. and 150° C.

If the temperature at which expansion is initiated is lower than 60° C., it may be necessary, according to the methods of the present invention, to cool down the hydrogel. Hence, an initiation expansion temperature of less the 60° C. is inefficient. On the other hand, if the temperature at which expansion starts is higher than 150° C., then the expansion efficiency may be lowered. Since the evaporation of a water component of (A) in a hydrogel proceeds in advance during a heat dry step and flexibility of the hydrogel decrease when (B') starts expanding, the expansion efficiency may be lowered.

In cases where the maximum expansion temperature is less than 80° C., or more than 180° C., the same phenomenon as described above can be generated and is not preferable.

Examples of the gases or volatile compounds which can be contained inside the filler (B2') include compounds having a boiling point, under normal pressure, of 150° C. or less, preferably 120° C. or less, and more preferably 100° C. or less. If the boiling point is higher than 150° C., it is economically inefficient because the temperature at which (B2') starts to expand becomes high. Consequently, a high temperature is required for a heating process in the manufacturing method of the present invention. In addition, it is possible that the degree of enhancement of the absorption speed of the resulting absorbent composition is lowered due to insufficient thermal expansion.

Examples of the gases or volatile compounds which can be contained inside the (B2') include, for instance, isobutane, isopentane, petroleum ether, n-butane, n-pentane, n-hexane, cyclopentane, cyclohexane, trichlorofluoromethane, dichlorofluoromethane, butene, methylenechloride and so forth. These can be used in combination. Among them, isobutane, isopentane, n-butane, n-pentane, and petroleum ether are preferable.

The particle size of (B2') is not particularly limited, however, it is generally 1 to 150 μm, and preferably 1 to 100 μm. If the particle size of (B2') is 150 μm or less, the uniformity obtained when (B2') is mixed with (A) in a hydrogel and the absorption speed of the resulting water absorbent is effectively improved according to the manufacturing methods of the present invention.

The magnitude of volume of (B2') to which it expands is preferably 10 times or more, and more preferably 30 times or more. If the magnitude to which the volume of(B2') expands is 10 times or more, the absorption speed of the resulting water absorbent is effectively improved due to a high expansion rate of (A).

Examples of the thermal expansile hollowed fillers (B2') that can be used in the present invention include Matsumoto microsphere F-20, F-30, F-40, F-50, F-80S, F-82, F-85, F-100, F-30VS, F-80GS, F-80VS, F-100SS, F-1300, F-1400 and so forth manufactured by Matsumoto Yushi Co., and Expansel 820,642, 551,461, 051, 091 and so forth manufactured by Japan ferrite Co. Two or more of these can be used in combination.

In the water absorbents [1] and [2] according to the present invention, the mass ratio between (A) and (B1) or (A) and (B2) is preferably 100:(0.05 to 10), more preferably 100: (0.10 to 7), and most preferably 100: (0.50 to 5). When the ratio of (B1) or (B2) is 100:0.05 or more, an enhancement of the absorption speed is realized. On the other hand, if the ratio is 100:10 or less, the absorption speed is improved and the mechanical strength of particles of the resulting water absorbent composition becomes sufficient to practical use. In addition, enhancement of the absorption speed of the resulting absorbent composition under applied pressure is also realized.

② when the apparent density is more than 0.1 g/cm³ but 5 g/cm³ or less (a micro-filler of this size is hereinafter referred to as a micro-filler (B3)) The apparent density of (B3) is generally greater than 0.1 g/cm³ but 5 g/cm³ or less, preferably between 0.15 g/cm³ and 4 g/cm³, and more preferably between 0.3 g/cm³ and 4 g/cm³.

When the apparent density of (B3) is 5 g/cm³ or less, a large increase in volume of the resulting absorbent composition is observed. Furthermore, the absorption speed, especially diffusive absorption speed, of the resulting absorbent composition is improved.

On the other hand, when the apparent density of (B3) is greater than 0.1 g/cm³, sufficient increase of the volume of the resulting absorbent composition is obtained. Furthermore, the absorption speed, especially the diffusive absorption speed, is not lowered. In addition, the particle strength is further enhanced so that no dust is generated because of destruction of the particles due to mechanical shear, collision or friction.

The particle size of (B3) is generally 0.001 μm to 200 μm, preferably 0.005 μm to 150 μm, and more preferably 0.01 μm to 100 μm. Note that the term "particle size" herein used means not only the particle size of the original particle but also the particle size of agglutinated or granulated particles. When the particle size of (B3) is 200 μm or less, the diffusive absorption speed of the resulting absorbent composition is efficiently improved since excellent uniformity is obtained when (B3) is mixed with a hydrogel of (A). On the other hand, if the particle size is 0.001 μm or more, an excellent uniformity is obtained when (B3) is mixed with a hydrogel of (A) since the agglutination among (B3) is hardly generated.

The specific surface area of (B3) according to BET method is not particularly limited, however, it is generally 50 m²/g or more, preferably 100 m²/g or more, and more preferably between 150 and 1000 m²/g. The larger the specific surface area of the micro-filler, the larger the enhancement of the diffusive absorption speed of the resulting absorbent.

The materials of (B3) are not limited if it is water insoluble and non-reactive with the water absorptive resin, and can be an organic or inorganic material. Examples of the organic material include the same ones described above for (B1) and ones which can be obtained by co-polymerizing two or more of monomers forming these resins.

Polyethylene, polypropylene, polystyrene, poly-p-xylylene, and polybutadiene are preferable. The melting temperature of the material needs to be higher than the temperature used for a drying process so that the organic filler does not melt when hydrogel is dried. The melting temperature of an organic material is generally 130° C. or more, and preferably 150° C. or more.

Examples of the inorganic micro-fillers include both the natural inorganic materials and the synthetic inorganic materials, and can be the same ones described above for (B1). Two or more of these can be used in combination or two or more of these can be formed into a complex.

Among these examples, inorganic micro-fillers are preferable.

The shape of (B3) is not particularly limited and can be hollowed, porous, petal-shaped, agglutinated, or granulated. The hollowed shape and porous shape are preferable. Practical examples of the micro-filler (B3) include, for instance, Sankilite manufactured by Sanki Kako Kensetsu Co., Terafine manufactured by Ube Materials Co., Aerosyl 200 manufactured by Nippon Aerosyl Co., Flowlight and Fineseal manufactured by Tokuyama Co., and Kyowado or Kyowa Kagaku Co.

The amount of (B3) with respect to (A) is generally 0.05 to 10% by mass, preferably 0.1 to 7%, and more preferably 0.2 to 5%. When the amount added is 0.05% or more, a large degree of enhancement is obtained in not only the diffusion absorption speed but also the mechanical strength of the resulting water absorbent particles, and further the absorption efficiency, amount of retention and amount of absorption under applied pressure are not lowered.

Methods for Producing the Absorbent Composition of the Present Invention

A method [3] according to the present invention is a method for producing a water absorptive resin (A) containing a built-in micro-filler (B) wherein the micro-filler (B) is mixed with the water absorptive resin (A) having been not yet dried after polymerization then the mixture is dried and ground. According to the method [4] of the present invention, the particles of (A) containing a built-in (B) are further subjected to a crosslinking process in the presence of a crosslinking agent so that the surface (and the proximity thereof) of the particles is crosslinked.

In the method [3] of the present invention, the micro-filler (B1) or (B3) is mixed in the water absorptive resin (A) at any stage between prior to a polymerization process of (A) and prior to a drying step of the mixture of (A) and (B1) or (B3). It is preferable that the micro-filler (B1) or (B3) is added to a hydrogel of (A), i.e., after the polymerization of (A), and then the mixture is dried to obtain an absorbent composition. This is because a larger degree of enhancement of the absorption speed is realized when (B1) or (B3) is added to (A) in a hydrogel because (B1) or (B3) is contained inside the water absorptive resin particles.

(B1) or (B3) can be added in the form of powder, aqueous slurry or aqueous dispersion. However, it is preferable to add (B1), as aqueous slurry or aqueous dispersion, to the hydrogel homogeneously in order to realize a larger degree of enhancement of the uniformity and absorption speed of the water absorptive composition.

Also, the percentage of the water content in the mixture of the hydrogel of (A) and (B1) or (B3) is preferably 2 to 10 times that of the solid components of (A). If the percentage is less than 2 times, a lower degree of uniformity is obtained during a mixing step and a lower degree of enhancement of the absorption speed of the resulting absorbent composition can result. If the percentage is more than 10 times, then, a longer time is required for drying the composition. This longer time is not economical.

A conventional kneader can be used for homogeneously dispersing (B1) or (B3) in the hydrogel of (A). Examples of such device include a double arm kneader, an internal mixer (banbury mixer), a self-cleaning type mixer, a gear compounder, a screw type extruder, a screw type kneader, mincer and so forth. These devices can be used in combination.

Temperature for drying the hydrogel type mixture, to which (B1) or (B3) is added, is generally 60 to 230° C., preferably 100 to 200° C., and more preferably 105 to 180° C. If the drying temperature is lower than 60° C., it is not economical because it takes very long time to dry the mixture. On the other hand, if the temperature is higher than 230° C., the absorption performance and the absorption speed or the resulting absorbent may be lowered due to possible side reactions and a decomposition of the resin.

Conventional devices can be used for drying the mixture having the hydrogel of (A) and (B1) or (B3). Examples of such a device include, for instance, a drum dryer, a parallel flow band dryer (a tunnel dryer), a through-flow band dryer, a blow flow (nozzle jet) dryer, a box type hot air dryer, an infrared dryer and so forth. The heat source is not particularly limited. A plurality of these dryers can be used in combination.

The water absorbent composition according to the present invention can be obtained by drying and grinding the (A) containing a built-in (B1) or a built-in (B3), adjusting the particle size thereof and subjecting the resulting composition to a crosslinking process. At the crosslinking process the surface (and the proximity thereof) of the particles of water absorbent composition is crosslinked by using a crosslinking agent. The crosslinking agent has at least two functional groups which can be reacted with acid groups such as a carboxyl group and/or its salt.

Such surface crosslinked type water absorbents are suitable for the present invention because it has a larger gel strength and an excellent absorption performance and absorption speed under not only normal pressure but also applied pressure.

Examples of the crosslinking agents used at surface crosslinking process include, for instance, polyglycidyl ether compounds (e.g. ethyleneglycol diglycidyl ether, glycerol 1,3-diglycidyl ether, glycerol triglycidyl ether, poly (ethyleneglycol) diglycidyl ether, polyglycerol polyglycidyl ether and so forth); polyol compounds (e.g. glycerol, ethyleneglycol, polyethyleneglycol and so forth); polyamine compounds (e.g. ethylene diamine, diethylene triamine and so forth); polyamine type resins (e.g. polyamide polyamine epichlorohydrin resin, polyamine epichlorohydrin resin and so forth), ethylenecarbonate, aziridine compounds, polyimine compounds and so forth.

The amount of crosslinking agent used for surface crosslinking is not particularly limited and can be varied in accordance with the type of the crosslinking agent used, the condition used for crosslinking, the objective performance and so forth. However, the amount is generally 0.001 to 3% by weight, preferably 0.01 to 2% by weight, and more preferably 0.05 to 1% by weight with respect to the water absorptive composition. If the amount of crosslinking agent is less than 0.001% by weight, the resulting water absorptive resin has substantially the same performance as water absorptive resins that are not subjected to a crosslinking treatment. On the other hand, if the amount is greater than 3% by weight, the absorption performance tends to be lowered and, hence, not preferable.

Additives and extending agents, if necessary, can be added to the mixture of (A) and (B1) or (B3) in a hydrogel. Examples of such include residual monomer reducers (for instance, sodium sulfite, hydrogen peroxide and so forth), antibacterial agents (for instance, quaternary ammonium salts, chlorohexizin compounds, metallic salt type antibacterial agents and so forth), preservatives, fragrances, deodorants, colorants, antioxidants, silica, zeolite and so forth. These additives can be added during or after the drying step of the hydrogel mixture.

The apparent density of the absorbent composition can be decreased, depending on the amount of (B1) or (B3) added, to one fourth of that of a composition not containing any (B1) nor (B3) because the density of (B1) or (B3) is low. Because in case of (B3), the surface area per unit weight of the composition increases significantly and the absorption speed, especially the diffusive absorption speed is enhanced, and further the mechanical strength and handling characteristics of the particles are improved.

When the thermal expansile hollowed filler (B2') is used, (B2') can be added in any steps between prior to polymerization to the water absorptive resin (A), i.e., a preparatory step for materials used for the polymerization and so forth and prior to the drying step. It is preferable that it is added to and mixed with (A) in a hydrogel after the polymerization step and before the drying step thereof. This is because the hydrogel of (A) is flexibly suited for expansion. Furthermore, it is possible to increase surface area of (A) by thermal expansion of volume during the drying step to be carried out thereafter. In addition, the volume expansion can be achieved in more uniform manner by using a crosslinking agent when (B') is added to the hydrogel polymer (A) after the polymerization step and before the drying step.

(B2') can be added in any form such as powder, aqueous slurry, and aqueous dispersion. However, it is preferable that an aqueous slurry or aqueous dispersion form of (B2') be added homogeneously to the hydrogel in order to improve uniformity in expansion and the absorption speed of the resulting water absorptive composition.

Also, the percentage of water content in the mixture of the (A) and (B2') hydrogel is equal to the case of the mixture of (A) and (B1) or (B3).

The same devices used for mixing and homogeneously dispersing (B1) or (B3) with (A) in the above-mentioned manufacturing method can be employed as a kneader device. The kneader device would mix and homogeneously disperse (B2') with the (A) in a hydrogel.

Temperature for drying the hydrogel type compound, to which (B2') has been added, is similar to the temperatures used for drying the hydrogel type compound containing a built-in (B1) or a built-in (B3) as explained above.

When an inflammable compound is contained inside (B2'), a direct heating type heat source is not preferable. However, if the compound is non-inflammable, type of heat source is not particularly limited. A plurality of these dryers before mentioned can be used in combination.

The water absorbents according to the present invention can be obtained, if necessary, by crosslinking the surface (and the proximity of the surface) of the absorbent particles obtained by grinding and adjusting the particle size of the above-mentioned mixture after the drying step. The drying step uses a crosslinking agent having at least two functional groups which can be reacted with a carboxyl group and/or its salt. Such a surface crosslinked type water absorbent is suitable for the present invention because it has a larger mechanical strength of gel and excellent absorption performance and absorption speed under not only normal pressure but also applied pressure.

The same crosslinking agents used for surface crosslinking in the aforementioned manufacturing method of the present invention can be employed using the same amount.

Similarly, additives and extending agents mentioned above, if necessary, can be added to the mixture of (A) and (B2'). These additives can be added during or after the drying step of the hydrogel mixture.

Shape and Particle Size Distribution

A suitable form for the absorbent composition according to the present invention is a grain form. It can be, for example, a crushed grain, which is obtained via a drying-grinding process after polymerization in an aqueous solution. It can also be a spherical type grain obtained by using a reverse phase suspension polymerization method.

The average particle size of the absorbent composition [1] of the present invention is generally 200 $\mu$m to 700 $\mu$m, and preferably 250 $\mu$m to 600 $\mu$m. Also, the particle size distribution between 1000 $\mu$m and 100 $\mu$m is generally 90% by mass or more and preferably 95% by mass or more.

When the average particle size is 700 $\mu$m or less, or the content of particles having size of 1000 $\mu$m or less is 90% by mass or greater, the absorption speed, especially the diffusive absorption speed in case of (B3), of the resulting absorbent is improved. On the other hand, when the average particle size is 200 $\mu$m or more, or the content of having size is of 100 $\mu$m or more is 90% by mass or greater, then it is easy to handle the particles, and a constant amount of the particles can be supplied by a disseminating machine, and the operation environment is not deteriorated because no dust is generated.

Specific Surface Area

The absorbent composition [1] according to the present invention is characterized by an improvement of 10% or more of its specific surface area as compared with (A) that does not contain a built-in (B). Here, the specific surface area is a value that is measured by using the BET method. Hence, the specific surface area of the absorbent composition of the present invention is improved by 10% or more with respect to that of (A) without (B).

In addition, the specific surface area of the absorbent composition [1] of the present invention having particle size of 150 $\mu$m to 500 $\mu$m is preferably 0.1 m$^2$/g or more.

Bulk Density

The bulk density of the absorbent composition [1] of the present invention is generally 0.1 to 0.7 g/cm$^3$, preferably 0.1 to 0.55 g/cm$^3$, and more preferably 0.2 to 0.5 g/cm$^3$. When it is 0.7 g/cm$^3$ or less, the effect of increasing the surface area per unit mass becomes sufficient. Note that the bulk density is a value measured based on JIS K3362.

Rupture Stress

The rupture stress of the absorbent composition [1] of the present invention when it is in a dry state having a water content of 1.5% or less is generally 10 N/m$^2$, preferably 20 N/m$^2$, and more preferably 25 N/m$^2$. The rupture stress tends to be increased as the water content of the composition is increased. The method used for measuring the rupture stress will be described later.

Absorption Speed, Diffusive Absorption Speed, Absorption Amount under Applied Pressure As described above, the specific surface area of the absorbent composition [1] of the present invention is improved. Thus, the absorption speed (time required for absorbing a certain amount) for physiological saline, especially the diffusion absorption speed in case of (B3), is improved as compared with that of (A) without (B). That is, the absorption speed for physiological saline of the absorbent composition [1] of the present invention is preferably reduced to 80% or less of the absorption speed for physiological saline of (A) not containing a built-in (B). In other words, the time to absorb a certain amount of the physiological saline of the absorbent composition [1] of the present invention is preferably reduced to 80% or less as compared to that of (A) without (B).

The absorption speed of the absorbent composition [1] of the present invention is preferably 25 seconds or less, and more preferably 20 seconds or less. The absorbent composition containing (B3), in particular, has an improved diffusion absorption speed of 25 to 65 ml/g, preferably 28 to 60 ml/g for 0.9% physiological saline. The improved diffusion absorption speed is effective to improve a feeling of dryness and/or to decrease leaking when applied to sanitary products such as disposable diapers.

In addition, the absorbent composition [1] of the present invention obtained by surface crosslinking has an improved absorption amount under applied pressure. Furthermore, the absorbent composition [1] of the present invention is capable of achieving the absorption speed of 25 seconds or less, preferably 20 seconds or less, for physiological saline while absorbing an amount of 25 g/g or more, preferably 28 g/g or more, for physiological saline under the applied pressure of 20 g/cm$^2$. Especially, the water absorbent containing (B3) has an improved diffusion absorption speed and initial amount of absorption under applied pressure. The water absorbent containing (B3) is capable of achieving the diffusive absorption speed of 25 to 65 ml/g, preferably 28 to 60 ml/g, for 0.9% physiological saline with the initial amount of absorption under applied pressure of 18 to 40 g/g, preferably 25 to 40 g/g, for 0.9% physiological saline. It is, therefore, effective in further increasing a feeling of dryness and further reducing lcaking when applied to sanitary products such as disposable diapers.

Note that the absorption speed, the diffusive absorption speed and the absorption amount under applied pressure are values measured using methods which will be described later.

Surface Active Agent Treatment

The absorbent composition [2] of the present invention is the absorbent composition which a surface active agent (C) is added to the surface of the above-mentioned absorbent composition [1].

Accordingly, physical properties such as the shape, particle size distribution, specific surface area, bulk density and so forth of the absorbent composition [2] of the present invention are basically the same as those of the absorbent composition [1]. Furthermore, the quick absorption speed that is a characteristic of the composition [1] is also maintained in the composition [2].

Types of the surface active agent (C) are not particularly limited and any of nonionic surface active agents, anionic surface active agents, cationic surface active agents and an ampholytic surface active agents can be employed.

Examples of the nonionic surface active agents include compounds in which ethylene oxide and/or propylene oxide is added (if both ethylene oxide and propylene oxide are used, it is a random or block addition) to an active hydrogen containing compound such as alkyl phenols, aliphatic alcohols, carboxylic acids, aliphatic amines, aliphatic amides, hydroxy denatured or amine denatured polysiloxane, polyalcohols which are partially esterified by fatty acids and so forth. One or more of these can be used in combination.

Examples of the nonionic surface active agents include the followings:
- ◎ C8–C24 alkyl phenols added with ethylene oxide and/or propylene oxide;
- ◎ C10–C24 aliphatic alcohol added with same compounds,
- ◎ C10–C24 fatty acids added with same compounds,
- ◎ C10–C24 aliphatic amines added with same compounds;
- ◎ C10–C24 aliphatic amides added with same compounds;
- ◎ polyoxyethylene denatured silicone oils; and
- ◎ C3–C6 polyalcohols which have been partially esterified by
- ◎ C10–C24 fatty acids, or compounds thereof further including 2–20 moles of ethylene oxide and/or propylene oxide on the partially esterified portion.

Examples of the anionic surface active agents include alkali metal salts of (C8–C24)-alkylsulfonic acid, alkali metal salts or trialkanol amine salts of (C8–C24)-alkylsulfate, diesters of sulfosuccinic acid, sulfosuccinate monoesters, (C8–C24)-alkylaryl sulfonic acids, sulfuric halfesters of products of which ethylene oxide is added to alkylphenol or aliphatic alcohol and so forth. Two or more of these anionic surface active agents can be used together or can be used with the nonionic surface active agents described above.

Examples of cationic surface active agents include a salt of aliphatic amines, quaternary aliphatic aminoesters, quaternary aliphatic aminoamides, addition products of an alkylene oxide and an aliphatic amine or a salt of aliphatic amine, long chain (C10–C22) alkyl benzylmethyl ammonium compounds and so forth.

Examples of the ampholytic surface active agents include compounds having at least one cationic group (for instance, a quaternary ammonium group) and anionic group (for instance, a carboxylate group and a sulfate group) in the same molecule, more specifically, dimethylcarboxylathyl fatty acid-alkylamideammonium betaines, 3-(3-fatty acid amid-propyl)dimethylammonium-2-hydroxypropane sulfonates and so forth.

Among these surface active agents, nonionic surface active agents having HLB (Griffin) of 3 or more, especially between 8 and 14, are preferable. Here, HLB is an index which indicates the balance of a surface active agents in terms of hydrophilic property and lipophilic property. The index can be controlled by the type and the number of functional groups, or mole number or molecular weight of added alkylene oxide.

The absorbent composition [2] of the present invention can be obtained by further adding the surface active agent (C) on the surface of the absorbent composition [1] which is obtained by the manufacturing methods described in [3] or [4] above.

The amount of the surface active agent (C), based on the mass of the absorbent composition [1], is generally 0.1 to 5%, preferably 0.1 to 3%, more preferably 0.2 to 2%. When the amount of (C) is 0.1% or more, a composition that has an excellent absorption speed for blood can be obtained because the effect of treating with (C) is sufficient and the improvement in affinity between the resulting composition and blood is obtained. On the other hand, if the amount of (C) is 5% or less, not only the absorption speed can be improved but also particle flowability of the resulting composition can be increased. Furthermore, problems related to particle handling can be eliminated.

The surface active agent (C) is preferably attached to the surface of the absorbent composition [1] when it is applied to the surface. If the surface active agent has permeability, it further permeates inside the composition.

Methods for adding the surface active agent (C) to the absorbent composition [1] are not particularly limited. For example, the surface active agent (C) can be mixed with the absorbent composition using a conventional mixing device. The surface active agent (C) can be undiluted or diluted using water or an aqueous solution.

Examples of the mixing devices include a V-type mixer, ribbon blender, turbulizer, almighty mixer, nauter mixer, fluidized mixer, spray mixer, line blender, continuous mixer, banbury mixer, mortar mixer and so forth. These can be used in combination.

Absorption Speed for Sheep Blood

The composition [2] of the present invention has an absorption speed for sheep blood of generally 30 seconds or less, preferably 25 seconds or less. The composition [2] of the present invention has a retention amount, after swelling in sheep blood for 30 minutes, of generally 20 g/g or more, preferably 23 g/g or more.

The composition [2] of the present invention possesses the balance of the absorption properties (the absorption speed and the amount of retention). Therefore, the composition [2] of the present invention is effective, compared with conventional water absorptive resins, in improving the amount of retention and a feeling of surface dryness, and reducing leaking when it is applied to various absorption products. These absorption products include sanitary napkins, panty liners, tampons, under-pads for operations, mats for a delivery beds, dressing materials for protecting a cut portion and so forth. The composition [2] of the present invention, however, is especially effective when applied to sanitary napkins.

Also, when the surface of the composition [2] is crosslinked according to the present invention, the amount of retention for sheep blood under applied pressure can be further improved to 20 g/g under a load of 20 g/cm$^2$.

The absorption speed for sheep blood, the amount of retention after swelling in sheep blood for 30 minutes, the amount of retention for sheep blood under applied pressure, the surface dryness of a napkin and the amount of retention of a napkin, are values measured by using methods which will be described later.

Note that artificial blood has been conventionally used for evaluating the absorption properties of water absorptive resins. An example of artificial blood is an aqueous solution containing about 0.9% of sodium chloride, about 0.4% of sodium bicarbonate, about 30% of glycerol, and about 0.18% of sodium carboxymethylcellulose, and, if necessary, surface active agents and coloring agents are added. There is a large difference in the absorption property when the artificial blood is used and when real blood (human blood, human menstrual blood, cattle blood, sheep blood and so forth) is used. Hence, it is necessary to use real blood for examining absorption properties for blood. This is because about 45 mol % of high molecular weight organic substances such as hemocytes, hemoglobin, cytoplasm, and protein components are contained in real blood.

Absorbent Products

The absorbent products according to the present invention include an absorption layer and a surface protection sheet. The absorption layer includes absorbent composition [1] or [2] of the present invention and fibrous material. The surface protection sheet has a water permeability portion to cover the absorption layer. The surface protection sheet, in cases of diaper for adults or infants or sanitary products, has, from the points of view of usage, a non-water permeable sheet which is normally located outside and a water permeable sheet which is preferably located inside. The absorption layer is preferably located in between the two sheets. The two sheets are joined preferably along their edges to form an absorbent product. In addition to such absorption layers located between the two sheets, a water absorption sheet, a liquid diffusion sheet and so forth can be used together if necessary.

Examples of the fibrous materials used for the absorption layer are not particularly limited and include known materials such as pulp, synthetic fibers, natural fibers, and mixtures of synthetic and natural fibers. The width and length of the fibrous materials are also not particularly limited.

EXAMPLES

The present invention will be further explained by using the following examples. However, the present invention is not limited to these particular examples by any means. Note that % used indicates % by mass unless otherwise indicated.

Methods for measuring the following items 1) to 13) for water absorptive resins, absorbent compositions, and napkins are shown below.

Items

Water absorptive resins and absorbent compositions:

1) Specific surface area

Absorbent compositions:

2) Absorption speed for 0.9% saline

3) Diffusive absorption speed

4) Amount of absorption under applied pressure for 0.9% saline

5) Amount of retention for 0.9% saline

6) Absorption speed for sheep blood

7) Amount of retention for sheep blood

8) Amount of absorption under an applied load for sheep blood

Napkins:

9) Absorption speed for sheep blood

10) Diffusion area of sheep blood

11) Surface dryness after the diffusion of sheep blood

12) Amount of retention for sheep blood

13) Rupture stress of particles

Measuring methods

1) Method for measuring specific surface area:

A specific surface area was measured by B.E.T 1 point method using (Kansobu QS-19) manufactured by Yuasa Ionisc Co. Conditions used for the measurement were measuring He/Kr=99.1/0.1 vol % gas, and calibrating $N_2$ gas, and a standard cell was used. Samples used for the measurement were pre-adjusted to 30 to 100 mesh.

2) Method for measuring the absorption speed of absorbent compositions:

A sample of an absorbent composition (2.00g) adjusted to particle size of 30 to 60 mesh by using a JIS standard strainer was prepared.
Saline (0.9% by mass, 50 g) was added to a beaker (100 ml, flat bottom) contained a magnet (diameter φ at central portion of 8 mm, diameter φ at both ends of 7 mm, length of 30 mm, coated by fluorine-contained resin to be thick in the center). The beaker was placed on the center portion of a magnetic stirrer equipment. The rotation of the magnetic stirrer was adjusted to 600±30 per minute and it was confirmed that a stable swirl of saline was formed.

The measurement was started, using a timer, immediately after the sample was added to saline of a position as close as, but not contacting, the inner surface of the beaker. The procedures so far are in accordance with JIS K7224.

The end point of the measurement was defined as when the swirl disappeared and the liquid surface became horizontal. The absorption speed was defined as time in seconds required from the start of the measurement to the end point.

3) Method for measuring the diffusive absorption speed of absorbent compositions:

A sample of an absorbent composition (0.10g) adjusted to a particle size of 30 to 60 mesh using a JIS standard strainer was prepared.

A device shown in FIG. 1 was placed on a flat surface of a table. It was confirmed that the position of a duct 5 and that of the upper surface of a plate 6 were horizontal.

A stop cock 1 of a burette 4 and a stop cock 2 were closed and 0.9% by mass of physiological saline was added to the burette 4 from the top. Then a stop cock 3 at the upper portion of the burette 4 was closed and the volume of the physiological saline in the burette was measured prior to opening the stop cock 1 and the stop cock 2. A plain cloth 7 made of nylon mesh (5 cm×5 cm, 63 μm quadrilateral unit section) was placed on the plate 6 having a hole of 3 mm diameter and a sample 8 was placed on the nylon mesh 7. The measurement was started immediately after placing the sample 8 on the mesh 7 and the sample 8 started to absorb saline. After 2 minutes, the volume of the saline in the burette 4 was measured and the amount of absorption was calculated. A value obtained by multiplying the calculated value by 10 is used as the diffusive absorption speed.

4) Method for measuring amount of absorption under applied pressure of absorbent composition:

Sample of absorbent composition (0.10 g) adjusted to a particle size of 30 to 60 mesh by using a JIS standard strainer was put in a cylindrical plastic tube (inner diameter φ of 30 mm, height of 60 mm). The cylindrical plastic tube had a nylon mesh of 250 mesh attached at the bottom, and flattened.

A weight of outer diameter φ of 30 mm was put on the absorbent composition so that it applied a load of 20 g/cm² to the composition. The plastic tube containing the absorbent composition was placed, with the nylon mesh side thereof faces downward, in a Petri dish (diameter φ of 12 cm) containing 60 ml of 0.9% by mass saline. After 5 minutes and 60 minutes, a measurement was taken showing that the mass of the absorbent composition increased by absorbing 0.9% saline. A value obtained by multiplying the measured value after 5 minutes by 10 is used as an initial amount of absorption under applied pressure for 0.9 saline. A value obtained by multiplying the measured value after 60 minutes by 10 is used as the amount of absorption under applied pressure.

5) Method for measuring the amount of retention of absorbent compositions:

A sample of an absorbent composition (1.00 g) was put in a tea bag (20 cm in length, 10 cm in width) and immersed in saline (0.9% by mass, 500 ml) for 60 minutes to absorb saline. The sample of absorbent composition had been adjusted to a particle size of 30 to 60 mesh by using a JIS standard strainer. The tea bag (20 cm in length, 10 cm in width) was made of nylon mesh of 250 mesh. The tea bag was hanged for 15 minutes to drain water and then centrifuged (150 G, 90 sec.) to measure mass increase. This increased mass is used as the amount of retention for 0.9% by mass saline.

6) Method for measuring the absorption speed of absorbent compositions for sheep blood:

A sample of an absorbent composition (10 g) adjusted to a particle size of 30 to 60 mesh by using a JIS standard strainer was prepared. The sample (20 g) was put in a Petri dish (diameter φ of 12 cm) and flattened. Then, sheep blood (5 g, containing 3.8% citric acid, Towa Jyunyaku Co.) was poured onto the center of the sample. The time was measured from when pouling the blood in the sample commenced to the complete absorption of sheep blood by the sample. This value is used as the absorption speed for sheep blood.

7) Method for measuring the amount of retention of absorbent compositions for sheep blood:

A sample of absorbent composition (1.0 g) was put in a tea bag (20 cm in length, 10 cm in width) made of nylon mesh of 250 mesh and immersed in sheep blood for 30 minutes to absorb the blood and expand. The sample of absorbent composition had been adjusted to a particle size of 30 to 60 mesh by using a JIS standard strainer. The tea bag was hanged for 15 minutes to drain the liquid and then centrifuged (250 G, 2 min.) to measure mass increase. This increased mass is used as the amount of retention for sheep blood.

8) Method for measuring the amount of absorption of absorbent composition under an applied load for sheep blood:

A sample of an absorbent composition (0.1 g) was put in a cylindrical plastic tube (inner diameter φ of 30 mm, height of 60 mm) and flattened. The particle size of the sample had been adjusted to 30 to 60 mesh by using a JIS standard strainer. The cylindrical plastic tube had a nylon mesh of 250 mesh at the bottom. A weight with an outer diameter φ of 30 mm was put on the sample so that it applied a load of 20 g/cm² to the sample. The plastic tube containing the sample was placed, with the nylon mesh side thereof facing downward, in a Petri dish (diameter φ of 12 cm) containing 50 g of sheep blood. After 30 minutes, the mass of the sample, which increased by absorbing sheep blood, was measured. A value that is obtained by multiplying the measured value by 10 is used as the amount of absorption under an applied load.

9) Method for measuring the absorption speed of napkins:

Fluff pulp layer of a tsubo of 100 g/m² was cut to the size of 6 cm×15 cm. An absorbent composition sample (0.4 g) was uniformly applied on it. Another fluff pulp layer of the same tsubo and size was put on the top of that and they were pressed (10 kg/cm², 30 sec.) on a wire netting to form an absorption layer.

A model napkin was made by using a leak-preventing film and non-woven fabric made of rayon which is placed on the absorption layer, and heat sealing them along with the edges of the absorption layer. The size of the leak preventing film is which is a little larger than the absorption layer and placed underneath the absorption layer. The non-woven fabric is made of rayon that is placed on the absorption layer.

A hole of diameter 12 mm was made on the center of an acrylic plate. The area of the acrylic plate was the same as that of the absorption layer. A plate for pouring the blood was prepared by fixing a circular cylinder of inner diameter 12 mm (length of 10 cm) on the hole. This plate was placed on the model napkin and a load of 20 g was placed so that pressure was applied uniformly on the napkin. Sheep blood (5 g) was poured from the circular cylinder and the time was measured until all of blood (5 g) was absorbed. This measurement was repeated three times and the average value thereof is used as the absorption speed.

10) Method for measuring the diffusion area of napkins:

After each measurement of the absorption speed, the diffusion area of sheep blood on the absorption layer was measured. This was repeated three times and the average value thereof is used as the diffusion area.

11) Method for measuring the surface dryness of napkins:

After each measurement of the diffusion area, feeling of dryness on the surface of the model napkin was judged based on the tactile measurements of five persons. This was repeated three times and the average thereof was evaluated by using the following criteria:

⊚: excellent dry feeling;

◯: somewhat damp, but practically no problem;

Δ: a little seepage with a feeling of tackiness; and

X: a lot of seepage with accompanying tackiness.

12) Method for measuring the amount of retention of napkins:

A model napkin was soaked in an excess of sheep blood for five minutes to absorb the blood. After that, it was centrifuged (250 G, 2 min.), with the non-woven fabric side facing the outside, to obtain a mass increase. The first number after the decimal point of the obtained value was rounded and this value is used as the amount of retention.

13) Method for measuring the rupture stress of particles:

A sample of particles having the particle size of 425 to 500 μm was compressed using a creep meter (Yamaden Co.). The value at which the particles were broken is used as the rupture stress (N/m unit).

Example 1

Sodium acrylate (77 g), acrylic acid (22.8 g), N,N'-methylene bis-acrylamide (0.2 g) and deionized water (295 g) were put in a reaction container (1 liter) made of glass and the temperature of the mixture was maintained at 3° C. with stirring.

Nitrogen gas was purged from the mixture in order to decrease the amount of dissolved oxygen to 1 ppm or less. Afterwards, an aqueous solution of hydrogen peroxide (1%, 1 g), an aqueous solution of ascorbic acid (0.2%, 1.2 g), and an aqueous solution of 2,2'-azo-bis-amidinopropane dihydrochloride (2%, 2.8 g) were added and mixed to initiate a polymerization reaction. After five hours of polymerization, a hydrogel polymer (A1G) was obtained.

The hydrogel polymer (A1G) was cut to the size of 3 mm to 7 mm using an internal mixer. Afterwards, 100 g of 2% aqueous dispersion (B11) of Expansel 091DE (apparent density=0.03 g/cm³; particle size of 50 to 80 μm) was added and mixed to be homogeneous by using the internal mixer. After that the mixture was dried using a through-flow band dryer (150° C., air flow speed of 2.0 m/sec. Inoue Kinzoku Kogyo Co.). The resulting dried substance was ground so as to adjust the particle size to 20 to 100 mesh and an absorbent composition (1) was obtained.

On the other hand, after cutting the hydrogel polymer (A1G) to a size of 3 mm to 7 mm using an internal mixer, it was dried by using a through-flow band dryer (150° C., air flow speed of 2.0 m/sec.). The resulting dried substance was ground so as to adjust the particle size to 20 to 100 mesh and a water absorptive resin (A1) was obtained.

The specific surface area of the water absorptive resin (A1) and that of the absorbent composition (1) were measured and the increasing rates were calculated. Results are shown in Table 1. Also, results of the evaluation on the performance of the absorbent composition (1) are shown in Table 2.

Example 2

10% ethylene glycol diglycidyl ether in a water/methanol mixed solution (water/methanol=70/30) (2 g) was added to 100 g of the absorbent composition (1) being stirred at high speed. After that the composition was subjected to a thermal crosslinking process (140° C., 30 min.) to obtain an absorbent composition (2) of a surface crosslinked type.

On the other hand, 10% ethylene glycol diglycidyl ether in a water/methanol mixed solution (water/methanol=70/30) (2 g) was added to 100 g of the water absorptive resin (A1) prepared in Example 1 being stilted at high speed. The composition was subjected to a thermal crosslinking process (140° C., 30 min.) to obtain a water absorptive resin (A2) of a surface crosslinked type.

The specific surface area of the water absorptive resin (A2) and that of the absorbent composition (2) were measured and the increasing rates were calculated. Results are shown in Table 1. Also, results of the evaluation on the performance of the absorbent composition (2) are shown in Table 2.

Examples 3 and 4

A dried substance of particle size of 20 to 100 mesh (100 g) was thermally crosslinked in the same manner as in Example 2. An absorbent composition (3) and another absorbent composition (4) were obtained. The dried substance was obtained by using the same procedure in Example 1 except that the amount of the dispersion (B11) added was changed to 25 g or 250 g.

The specific surface area of each of the absorbent compositions (3) and (4) was measured and the increasing rates relative to the water absorptive resin 2) were calculated. Results are shown in Table 1. Also, results of the evaluation on the performance of the absorbent compositions (3) and (4) are shown in Table 2.

Examples 5 and 6

An absorbent composition (5) and another absorbent composition (6) were obtained by using the same procedure as in Example 1, except that the following dispersion (B12) or (B13) was used instead of the dispersion (B11) (the amount used was the same), and the same surface crosslinking method as in Example 2:

Dispersion (B12): 2% aqueous dispersion of Expansel 461DE (apparent density=0.06 g/cm$^3$; particle size of 20 $\mu$m to 40 $\mu$m), and Dispersion (B13): 2% aqueous dispersion of Expansel 551DE (apparent density=0.04 g/cm$^3$; particle size of 30 $\mu$m to 50 $\mu$m).

The specific surface area of each of the absorbent compositions (5) and (6) was measured and the increasing rates relative to the water absorptive resin (A2) were calculated. Results are shown in Table 1. Also, results of the evaluation on the performance of the absorbent compositions (5) and (6) are shown in Table 2.

Example 7

Sodium acrylate (77 g), acrylic acid (22.8 g), N,N'-methylene bis-acrylamide (0.2 g) and deionized water (293 g) were put in a reaction container (1 liter) made of glass and "Expansel 091DE" (2 g) was added by stirring. The temperature of the mixture was maintained at 3° C.

Nitrogen gas was purged from the mixture in order to decrease the amount of dissolved oxygen to 1 ppm or less. Afterwards, an aqueous solution of hydrogen peroxide (1%, 1 g), an aqueous solution of ascorbic acid (0.2%, 1.2 g), and an aqueous solution of 2,2'-azo-bis-amidinopropane dihydrochloride (2%, 2.8 g) were added and mixed to initiate a polymerization reaction. After five hours of polymerization, a hydrogel polymer mixture (AB1G) was obtained.

After cutting the hydrogel polymer mixture (AB1G) using an internal mixer, it was dried using a through-flow band dryer (150° C., air flow speed of 2.0 m/sec.). The resulting dried substance was ground so as to adjust the particle size to 20 to 100 mesh. Afterwards, 10% ethylene glycol diglycidyl ether in a water/methanol mixed solution (water/methanol=70/30) (2 g) was added to 100 g of the ground and dried substance being stilted at high speed. The composition was subjected to a thermal crosslinking process (140° C., 30 min.) to obtain an absorbent composition (7) of a surface crosslinked type.

The specific surface area of the absorbent composition (7) was measured and an increasing rate of the specific surface area relative to the water absorptive resin (A2) was calculated. Results are shown in Table 1. Also, results of the evaluation on the performance of the absorbent composition (7) are shown in Table 2.

Example 8

Acrylic acid (81.8 g), N,N'-methylene bis-acrylamide (0.2 g) and deionized water (241 g) were put in a reaction container (1 liter) made of glass and the temperature of the mixture was maintained at 3° C. with stirring.

Nitrogen gas was purged from the mixture in order to decrease the amount of dissolved oxygen to 1 ppm or less. Afterwards, an aqueous solution of hydrogen peroxide (1%, 1 g), an aqueous solution of ascorbic acid (0.2%, 1.2 g), and an aqueous solution of 2,2'-azo-bis-amidinopropane dihydrochloride (2%, 2.8 g) were added and mixed to initiate a polymerization reaction. After five hours of polymerization, a hydrogel polymer was obtained.

During a cutting process of the hydrogel polymer using an internal mixer, 30% sodium hydroxide aqueous solution (109.1 g) was added and mixed to obtain a hydrogel polymer (A3G) in which 72 mol % of carboxylic acids was neutralized.

The same 2% aqueous dispersion (B11) (100 g) used in Example 1 was added to the hydrogel polymer (A3G). After being homogeneously mixed using an internal mixer, it was dried by using a through-flow band dryer (150° C., air flow speed of 2.0 m/sec.).

The resulting dried substance was ground so as to adjust the particle size to 20 to 100 mesh. Afterwards, 10% ethylene glycol diglycidyl ether in a water/methanol mixed solution (water/methanol=70/30) (2 g) was added to 100 g of the ground and dried substance being stirred at high speed. The composition was subjected to a thermal crosslinking process (140° C., 30 min.) to obtain an absorbent composition (8) of a surface crosslinked type.

On the other hand, after the hydrogel polymer (A3G) was homogeneously mixed using an internal mixer, it was dried using a through-flow band dryer (150° C., air flow speed of 2.0 m/sec.). The resulting dried substance was ground so as to adjust the particle size to 20 to 100 mesh. Afterwards, 10% ethylene glycol diglycidyl ether in a water/methanol mixed solution (water/methanol=70/30) (2 g) was added to 100 g of the ground dried substance being stirred at high speed. The composition was subjected to a thermal crosslinking process (140° C., 30 min.) to obtain water absorptive resin (A3) of a surface crosslinked type.

The specific surface area of the water absorptive resin (A3) and that of the absorbent composition (8) were measured and the increasing rates of the specific surface area were calculated. Results are shown in Table 1. Also, results of the evaluation on the performance of the absorbent composition (8) are shown in Table 2.

Comparative Example 1

The water absorptive resin (A1) obtained in Example 1 was regarded as a comparative absorbent composition (c1) and its results of the evaluation on the performance are shown in Table 2.

Comparative Example 2

Water absorptive resin (A2) obtained in Example 2 was regarded as a comparative absorbent composition (c2) and its results of the evaluation on the performance are shown in Table 2.

Comparative Example 3

B11 (100 g) and deionized water (295 g) were added to the water absorptive resin (A1) obtained in Example 1. After being homogeneously mixed by using an internal mixer, it was dried using a through-flow band dryer (150° C., air flow speed of 2.0 m/sec.). The resulting dried substance was ground so as to adjust the particle size to 20 to 100 mesh and a comparative absorbent composition (c3) was obtained.

Results of the evaluation on the performance of the comparative absorbent composition (c3) are shown in Table 2.

Comparative Examples 4 and 5

A comparative absorbent composition (c4) and a comparative absorbent composition (c5) were obtained by surface crosslinking, in the same manner as in Example 2. 100 g of dried substance having a particle size of 20 to 100 mesh was obtained using the same procedure as in Example 1 except that the amount of the dispersion (B11) added was changed to 2 g or 600 g.

The specific surface area of each of the comparative absorbent compositions (c4) and (c5) were measured and the increasing rates of the specific surface area relative to that of the water absorptive resin (A2) were calculated. Results of the evaluation on the performance of the comparative absorbent compositions (c4) and (c5) are shown in Table 2.

Comparative Example 6

After cutting the hydrogel polymer (A1G), 2%, with respect to solid components of (A1G), of "Binihole AZ-S" was added. The hydrogel polymer (A1G) was obtained in Example 1 using an internal mixer to the size of 3 mm to 7 mm. "Binihole AZ-S" (decomposition temperature of 100° C., main components: azo-bis-isobutylonitrile, Eiwa Kasci Kogyo Co.) is a pyrolytic foaming agent. After they were mixed homogeneously by using an internal mixer, the mixture was dried by using a through-flow band dryer (150° C., air flow speed of 2.0 m/sec.). The resulting dried substance was ground so as to adjust the particle size to 20 to 100 mesh. Afterwards, 10% ethylene glycol diglycidyl ether in a water/methanol mixed solution (water/methanol=70/30) (2 g) was added to 100 g of the ground and dried substance being stirred at high speed. The composition was subjected to a thermal crosslinking process (140° C., 30 min.) to obtain a comparative absorbent composition (c6) of a surface crosslinked type.

The specific surface area of the comparative absorbent composition (c6) was measured and an increasing rate of the specific surface area relative to that of the water absorptive resin (A2) was calculated. Results are shown in Table 1. Also, results of the evaluation on the performance of the comparative absorbent composition (c6) are shown in Table 2.

TABLE 1

| | Water absorptive resin | | Absorbent composition | | Increasing rate of Specific surface area |
|---|---|---|---|---|---|
| | Mark | Specific surface area S1 | Mark | Specific surface area S2 | (s2 − s1)/s1 × 100 |
| Ex.1 | (A1) | 0.44 | (1) | 0.53 | 20.5 |
| Ex.2 | (A2) | 0.42 | (2) | 0.51 | 21.4 |
| Ex.3 | (A2) | 0.42 | (3) | 0.48 | 14.3 |
| Ex.4 | (A2) | 0.42 | (4) | 0.71 | 69.0 |
| Ex.5 | (A2) | 0.42 | (5) | 0.50 | 19.0 |
| Ex.6 | (A2) | 0.42 | (6) | 0.52 | 23.8 |
| Ex.7 | (A2) | 0.42 | (7) | 0.49 | 16.7 |
| Ex.8 | (A3) | 0.43 | (8) | 0.53 | 23.3 |
| C.Ex.3 | (A1) | 0.44 | (c3) | 0.48 | 9.1 |
| C.Ex.4 | (A2) | 0.42 | (c4) | 0.43 | 2.4 |
| C.Ex.5 | (A2) | 0.42 | (c5) | 1.12 | 166.7 |
| C.Ex.6 | (A3) | 0.42 | (c6) | 0.46 | 9.5 |

TABLE 2

| | Absorbent composition | Absorption speed (sec) | Initial absorbency under load (g/g) | Absorbency under load (g/g) | Retention (g/g) |
|---|---|---|---|---|---|
| Ex.1 | (1) | 17 | 14 | 17 | 53 |
| Ex.2 | (2) | 15 | 24 | 33 | 41 |
| Ex.3 | (3) | 19 | 23 | 34 | 41 |
| Ex.4 | (4) | 11 | 27 | 33 | 41 |
| Ex.5 | (5) | 18 | 23 | 34 | 41 |
| Ex.6 | (6) | 17 | 25 | 33 | 41 |
| Ex.7 | (7) | 16 | 24 | 33 | 41 |
| Ex.8 | (8) | 16 | 26 | 36 | 44 |
| C.Ex.1 | (c1) | 35 | 5 | 16 | 53 |
| C.Ex.2 | (c2) | 34 | 18 | 33 | 41 |
| C.Ex.3 | (c3) | 22 | 7 | 13 | 47 |
| C.Ex.4 | (c4) | 34 | 18 | 32 | 41 |
| C.Ex.5 | (c5) | 23 | 14 | 26 | 39 |
| C.Ex.6 | (c6) | 27 | 16 | 24 | 34 |

Example 9

The hydrogel polymer (A1G) was cut using an internal mixer to the size of 3 mm to 7 mm. Afterwards, 10 g of 20% aqueous dispersion of (B21) "Matsumoto Microsphere F-30 (initial expansion temperature of 85° C. to 90° C., maximum expansion temperature of 130° C. to 140° C., expansion rate of about 72 times) was added. After they were mixed homogeneously by using an internal mixer, the mixture was dried using a through-flow band dryer (150° C., air flow speed of 2.0 m/sec., Inoue Kinzoku Kogyo Co.). The resulting dried substance was ground so as to adjust the particle size to 20 mesh to 100 mesh and an absorbent composition (9) was obtained.

The specific surface area of the absorbent composition (9) was measured and an increasing rate of the specific surface area relative to that of the water absorptive resin (A2) was calculated. Results are shown in Table 3. Also, results of the evaluation on the performance of the comparative absorbent composition (9) are shown in Table 4.

Example 10

10% ethylene glycol diglycidyl ether in a water/methanol mixed solution (water/methanol=70/30) (2 g) was added to 100 g of the absorbent composition (9) being stirred at high speed. Afterwards, the composition was subjected to a thermal crosslinking process (140° C., 30 min.) to obtain an absorbent composition (10) of a surface crosslinked type.

The specific surface area of the absorbent composition (10) was measured and an increasing rate of the specific surface area relative to the specific surface area of the water absorptive resin (A2) that is a surface crosslinked type was calculated. Results are shown in Table 3. Also, results of the evaluation on the performance of the absorbent composition (10) are shown in Table 4.

Examples 11 and 12

An absorbent composition (11) and an absorbent composition (12) were obtained by surface crosslinking, in the same manner as in Example 10. 100 g of dried substance has a particle size of 20 to 100 mesh. The dried substance was obtained by using the same procedure as in Example 9 except that the amount of the dispersion (B21) added was changed to 2.5 g and 25 g, respectively.

The specific surface area of each of the absorbent compositions (11) and (12) were measured and the respective increasing rates of the specific surface area relative to the water absorptive resin (A2) which is a surface crosslinked type were calculated. Results are shown in Table 3. Also, results of the evaluation on the performance of each of the absorbent compositions (11) and (12) are shown in Table 4.

Examples 13 and 14

An absorbent composition (13) and an absorbent composition (14) were obtained by using the same procedure as in Example 9, except that instead of the dispersion (B21) an equal amount the following respective dispersion (B22) or (B23) was used, respectively. Surface crosslinking was in the same manner as that of Example 10:

Aqueous dispersion (B23): 20% aqueous dispersion of "Matsumoto Microsphere F-40" (initial expansion temperature of 100° C. to 105° C., maximum expansion temperature of 130° C. to 140° C., expansion rate of 46 times); and Aqueous dispersion (B24): 20% aqueous dispersion of "Matsumoto Microsphere F-20" (initial expansion temperature of 80 to 85° C., maximum expansion temperature of 105° C. to 115° C., expansion rate of about 43 times).

The specific surface area of the absorbent compositions (13) and (14) were measured and the respective increasing rates of the specific surface area relative to the water absorptive resin (A2) were calculated. Results are shown in Table 3. Also, results of the evaluation on the performance of each of the absorbent compositions (13) and (14) are shown in Table 2.

Example 15

Sodium acrylate (77 g), acrylic acid (22.8 g), N,N'-methylene bisacrylamide (0.2 g) and deionized water (293 g) were put in a reaction container (1 liter) made of glass and "Matsumoto Microsphere F-30" (2 g) was added with stirring. The temperature of the mixture was maintained at 3° C.

Nitrogen gas was purged in the mixture in order to decrease the amount of dissolved oxygen to 1 ppm or less. Afterwards, an aqueous solution of hydrogen peroxide (1%, 1 g), an aqueous solution of ascorbic acid (0.2%, 1.2 g), and an aqueous solution of 2,2'-azobisamidinopropane dihydrochloride (2%, 2.8 g) were added and mixed to initiate a polymerization reaction. After five hours of polymerization, a hydrogel polymer mixture (AB1) was obtained.

After cutting the hydrogel polymer mixture (AB1) using an internal mixer, they were dried using a through-flow band dryer (150° C., air flow speed of 2.0 m/sec.). The resulting dried substance was ground so as to adjust the particle size to 20 to 100 mesh. Afterwards, 10% ethylene glycol diglycidyl ether in a water/methanol mixed solution (water/methanol=70/30) (2 g) was added to 100 g of the ground dried substance being stirred at high speed. The composition was subjected to a thermal crosslinking process (140° C., 30 min.) to obtain an absorbent composition (15) of a surface crosslinked type.

The specific surface area of the absorbent composition (15) was measured and an increasing rate of the specific surface area relative to the water absorptive resin (A2) was calculated. Results are shown in Table 3. Also, results of the evaluation on the performance of the absorbent composition (15) are shown in Table 4.

Example 16

Using the same procedure as in Example 8, a hydrogel polymer (A2) in which 72 mol % of carboxylic acid had been neutralized was obtained.

After the same dispersion (B21, 10 g) used in Example 9 was added to the hydrogel polymer (A2) and homogeneously mixed, it was dried using a through-flow band dryer (150° C., air flow speed of 2.0 m/sec.). The resulting dried substance was ground so as to adjust the particle size to 20 to 100 mesh. Afterwards, 10% ethylene glycol diglycidyl ether in a water/methanol mixed solution (water/methanol= 70/30) (2 g) was added to 100 g of the ground and dried substance being stirred at high speed. The composition was subjected to a thermal crosslinking process (140° C., 30 min.) to obtain an absorbent composition (16) of a surface crosslinked type.

The specific surface area of the absorbent composition (16) was measured and an increasing rate of the specific surface area relative to the water absorptive resin (A3) of a surface crosslinked type was calculated. Results are shown in Table 3. Also, results of the evaluation on the performance of the absorbent composition (16) are shown in Table 4.

Comparative Examples 7 and 8

A comparative absorbent composition (c7) and a comparative absorbent composition (c8) were obtained by surface crosslinking, in the same manner as in Example 10. 100 g of dried substance having a particle size of 20 to 100 mesh was obtained by using the same procedure as in Example 9 except that the amount of the dispersion (B21) added was changed to 0.2 g or 60 g, respectively.

The specific surface area of each of the comparative absorbent compositions (c7) and (c8) were measured and the respective increasing rate of the specific surface area relative to the surface crosslinked type water absorptive resin (A2) were calculated. Results are shown in Table 3. Also, results of the evaluation on the performance of each of the comparative absorbent compositions (c7) and (c8) are shown in Table 4.

Co.; HLB=14) was added and mixed to obtain an absorbent composition (17) of the present invention. Results of the evaluation on the performance of the absorbent composition (17) are shown in Table 5.

Example 18

5% ethylene glycol diglycidyl ether in a water/methanol mixed solution (water/methanol=70/30) (2.5 g) was added to 100 g of the absorbent composition (9). The absorbent composition (9) was being stirred at high speed. The composition was subjected to a thermal crosslinking process (140° C., 30 min.) to obtain an absorbent composition (18') of surface crosslinked type. The absorbent composition (18') (100 g) was put in a V-type mixer (300 ml capacity). While it was rotated, 0.1 g of polyoxyethylene denatured silicone oil used in Example 17 was added and mixed to obtain an absorbent composition (18) of the present invention. Results of the evaluation on the performance of the absorbent composition (18) are shown in Table 5.

Examples 19 and 20

The absorbent composition (11) and the absorbent composition (12) were obtained using the same procedure as in Examples 11 and 12. Each of the absorbent composition (11) (100 g) and the absorbent composition (12) (100 g) was put in a V-type mixer (300 ml capacity). While it was rotated,

TABLE 3

| | Water absorptive resin | | Absorbent composition | | Increasing rate of Specific surface area |
|---|---|---|---|---|---|
| | Mark | Specific surface area S1 | Mark | Specific surface area S2 | (s2 − s1)/s1 × 100 |
| Ex.9 | (A1) | 0.44 | (9) | 0.58 | 31.8 |
| Ex.10 | (A2) | 0.42 | (10) | 0.57 | 35.7 |
| Ex.11 | (A2) | 0.42 | (11) | 0.50 | 19.0 |
| Ex.12 | (A2) | 0.42 | (12) | 0.72 | 60.0 |
| Ex.13 | (A2) | 0.42 | (13) | 0.53 | 26.2 |
| Ex.14 | (A2) | 0.42 | (14) | 0.54 | 28.6 |
| Ex.15 | (A2) | 0.42 | (15) | 0.51 | 21.4 |
| Ex.16 | (A3) | 0.43 | (16) | 0.60 | 39.5 |
| C.Ex.7 | (A1) | 0.42 | (c7) | 0.44 | 4.8 |
| C.Ex.8 | (A2) | 0.42 | (c8) | 1.10 | 162.2 |

TABLE 4

| | Absorbent composition | Absorption speed (sec) | Initial absorbency under load (g/g) | Absorbency under load (g/g) | Retention (g/g) |
|---|---|---|---|---|---|
| Ex.9 | (9) | 16 | 13 | 18 | 53 |
| Ex.10 | (10) | 14 | 25 | 34 | 41 |
| Ex.11 | (11) | 19 | 23 | 34 | 41 |
| Ex.12 | (12) | 11 | 28 | 33 | 41 |
| Ex.13 | (13) | 17 | 24 | 34 | 4i |
| Ex.14 | (14) | 16 | 26 | 34 | 41 |
| Ex.15 | (15) | 15 | 25 | 34 | 44 |
| Ex.16 | (16) | 15 | 27 | 37 | 44 |
| C.Ex.7 | (c7) | 34 | 19 | 32 | 41 |
| C.Ex.8 | (c8) | 21 | 15 | 27 | 38 |

Example 17

The absorbent composition (9) was obtained using the same procedure as in Example 9. The absorbent composition (9) (100 g) was put in a V-type mixer (300 ml capacity). While it was rotated, 0.1 g of polyoxyethylene denatured silicone oil ("Shinetsu Silicone KF-618", Shinetsu Kagaku 0.1 g of polyoxyethylene denatured silicone oil used in Example 17 was added and mixed to obtain an absorbent composition (19) and an absorbent composition (20) of the present invention. Results of the evaluation on the performance of these absorbent compositions are shown in Table 5.

Examples 21 to 24

The absorbent composition (2) and the absorbent composition (5) were obtained using the same procedure as in Examples 2 and 5. Also, the absorbent composition (13) and the absorbent composition (14) were obtained by using the same procedure as in Examples 13 and 14. Each of these absorbent compositions (2),(5), (13) and (14) (100 g each) was put in a V-type mixer (300 ml capacity). While it was rotated, 0.1 g of polyoxyethylene denatured silicone oil used in Example 17 was added and mixed to obtain absorbent compositions (21) to (24) of the present invention. Results of the evaluation on the performance of these absorbent compositions are shown in Table 5.

Examples 25 to 28

Absorbent compositions (25) to (28) were obtained using the same procedure as in Example 18 except that respective following surface active agents of the same amount were used instead of the polyoxyethylene denatured silicone oil.

Results of the evaluation on the performance of these absorbent compositions are shown in Table 5.

Used for the absorbent composition (25): Mixture of Polyoxyethylene lauryl ether and Polyoxyethylene myristyl ether ("Nonipol soft SS-50" Sanyo Chemical Industries, Ltd.; HLB=10.6).

Used for the absorbent composition (26): Polyoxyethylene nonylphenyl ether ("Nonipol 40" Sanyo Chemical Industries, Ltd.; HLB=8.9).

Used for the absorbent composition (27): Sodium sulfate of Polyoxyethylene lauryl ether ("Sandet EN" Sanyo Chemical Industries, Ltd.; an anionic surface active agent).

Used for the absorbent composition (28): Disodium lauroyl ethanolamide polyoxyethelene sulfosuccinate ("Beaulight A-5000" Sanyo Chemical Industries, Ltd.; an amphoteric surface active agent).

Example 29

The absorbent composition (15) was obtained using the same procedure as in Example 15. The absorbent composition (15) (100 g) was put in a V-type mixer (300 ml capacity). While the absorbent composition (15) was rotated, 0.1 g of polyoxyethylene denatured silicone oil used in Example 17 was added and mixed to obtain an absorbent composition (29) of the present invention. Results of the evaluation on the performance of the absorbent composition (29) are shown in Table 5.

Example 30

The absorbent composition (16) was obtained by using the same procedure as in Example 16. The absorbent composition (16) (100 g) was put in a V-type mixer (300ml capacity). While it was rotated, 0.1 g of polyoxyethylene denatured silicone oil used in Example 17 was added and mixed to obtain an absorbent composition (30) of the present invention. Results of the evaluation on the performance of the absorbent composition (30) are shown in Table 5.

TABLE 5

Bulk Density of Absorbent Compositions and Results of Evaluation of Absorbent Compositions by using Sheep Blood

| Examples | Absorbent composition | Bulk density (g/cm³) | Absorption speed for sheep blood (sec) | Retention after swelling in sheep blood for 30 min. (g/g) | Absorption for sheep blood under load (g/g) |
|---|---|---|---|---|---|
| 17 | (17) | 0.44 | 28 | 31 | 12 |
| 18 | (18) | 0.42 | 10 | 29 | 27 |
| 19 | (19) | 0.55 | 18 | 30 | 28 |
| 20 | (20) | 0.28 | 9 | 29 | 25 |
| 21 | (21) | 0.49 | 12 | 30 | 27 |
| 22 | (22) | 0.48 | 15 | 29 | 27 |
| 23 | (23) | 0.46 | 21 | 28 | 26 |
| 24 | (24) | 0.54 | 23 | 28 | 26 |
| 25 | (25) | 0.44 | 12 | 29 | 28 |
| 26 | (26) | 0.45 | 15 | 28 | 27 |
| 27 | (27) | 0.46 | 13 | 27 | 26 |
| 28 | (28) | 0.44 | 10 | 27 | 28 |
| 29 | (29) | 0.48 | 10 | 29 | 27 |
| 30 | (30) | 0.43 | 8 | 30 | 30 |

Comparative Example 9

The comparative absorbent composition (c1) obtained in Comparative Example 1 was used as a comparative absorbent composition (c9) and results of a measurement of bulk density and the evaluation using sheep blood are shown in Table

Comparative Example 10

The comparative absorbent composition (c2) obtained in Comparative Example 2 was used as a comparative absorbent composition (c10) and results of a measurement of bulk density and the evaluation using, sheep blood are shown in Table

Comparative Examples 11 to 16

Each absorbent composition (9) obtained in Example 9, absorbent composition (18') of a surface crosslinked type obtained in Example 18, absorbent compositions (2) and (5) obtained in the same manner as in Examples 2 and 5, respectively, and absorbent compositions (13) and (14) obtained in the same manner as in Examples 13 and 14, respectively, is used as comparative absorbent compositions (c11) to (c16). Results of these compositions are shown in Table 6.

Comparative Example 17

The comparative absorbent composition (c9) obtained in Comparative Example 9 was put in a V-type mixer (300 ml capacity). While it was rotated, 0.1 g of polyoxyethylene denatured silicone oil used in Example 17 was added and mixed to obtain a comparative absorbent composition (c17). Results of the evaluation on the performance of the comparative absorbent composition (c17) are shown in Table 6.

Comparative Example 18

After cutting the hydrogel polymer (AB1G) obtained in Example 15 using an internal mixer to a size of 3 mm to 7 mm, they were dried using a through-flow band dryer (150° C., air flow speed of 2.0 m/sec.). The resulting dried substance was ground so as to adjust the particle size to 20 to 100 mesh. This dried substance having an adjusted particle size was subjected to a surface crosslinking process, in the same manner as in Example 2, to obtain a comparative absorbent composition (c18). Results of the evaluation of the comparative absorbent composition (c18) are shown in Table 6.

Comparative Example 19

The hydrogel polymer (A1G) obtained in Example 1 was cut by using an internal mixer to a size of 3 mm to 7 mm. Afterwards, 2%, with respect to the solid components of(A1G), of "Binihole AZ-S" (decomposition temperature of 100° C., main components: azo-bis-isobutylonitrile, Eiwa Kasci Kogyo Co.) which is a pyrolytic foaming agent was added. After they were mixed homogeneously by using an internal mixer, the mixture was dried using a through-flow band dryer (150° C., air flow speed of 2.0 m/sec.). The resulting dried substance was ground so as to adjust the particle size to 20 to 100 mesh to obtain a comparative absorbent composition (C19). Results of the evaluation of the comparative absorbent composition (c19) are in Table 6.

Example 31

The hydrogel polymer (A1G) was obtained using the same procedure as in Example 1. After cutting the (A1G) to a size of 2 mm to 5 mm using an internal mixer, 0.1 g of ethylene glycol diglycidyl ether and 3 g of (B31) (Sankilite YO2, apparent density=0.66 g/cm$^3$; particle size=20 $\mu$m to 70 $\mu$m) were added. After they were mixed homogeneously by using an internal mixer, the mixture was dried by using a through-flow band dryer (150° C., air flow speed of 2.0 m/sec., Inoue Kinzoku Kogyo Co.). The resulting dried substance was ground so as to adjust the particle size to 20 to 100 mesh to obtain an absorbent composition (31).

The specific surface area of the absorbent composition (31) was measured and an increasing rate of the specific surface area relative to the water absorptive resin (A2) of a surface crosslinked type was calculated. Results are shown in Table 7. Also, results of the evaluation on the performance of the absorbent composition (31) are shown in Table 8.

The increasing rate of the specific surface area of the following absorbent compositions 32 to 38, respectively, was calculated in the same manner and results are shown in Table 7. Also, results of the evaluation on the performance of the absorbent compositions 32 to 38 are shown in Table 8.

Example 32

After cutting the hydrogel polymer (A1G) obtained in Example 1 to a size of 2 to 5 mm by using an internal mixer, the same amount of (B31) used in Example 31 was added. Then by using the same procedure as in Example 31, an absorbent composition of 20 to 100 mesh particle size was obtained. 10% ethylene glycol diglycidyl ether in a water/methanol mixed solution (water/methanol=70/30) (2 g) was added to 100 g of this composition being stilted at high speed and then the composition was subjected to a thermal crosslinking process (140° C., 30 min.) to obtain an absorbent composition (32) of a surface crosslinked type.

Examples 33 and 34

Surface crosslinked type absorbent compositions (33) and (34) were obtained by using the same procedure as in

TABLE 6

Bulk Density of Comparative Absorbent and
Results of Evaluation of Absorbent Composition using Sheep Blood

| Comparative Examples | Comparative absorbent | Bulk density (g/cm$^3$) | Absorption speed for sheep blood (sec) | Retention after swelling in sheep blood for 30 min. (g/g) | Absorption for sheep blood under load (g/g) |
|---|---|---|---|---|---|
| 9 | (c9) | 0.71 | 80 | 18 | 7 |
| 10 | (c10) | 0.68 | 72 | 23 | 22 |
| 11 | (c11) | 0.44 | 96 | 19 | 9 |
| 12 | (c12) | 0.43 | 47 | 25 | 26 |
| 13 | (c13) | 0.51 | 51 | 25 | 25 |
| 14 | (c14) | 0.48 | 60 | 25 | 25 |
| 15 | (c15) | 0.47 | 66 | 24 | 24 |
| 16 | (c16) | 0.53 | 68 | 24 | 24 |
| 17 | (c17) | 0.69 | 85 | 20 | 10 |
| 18 | (c18) | 0.47 | 50 | 24 | 25 |
| 19 | (c19) | 0.62 | 63 | 21 | 11 |

Example 32 except that the amount of (B31) added was changed to 1 g or 6 g, respectively.

Examples 35 and 36

An absorbent composition (35) and an absorbent composition (36) were obtained by using the same procedure as in Example 32 except that the same amount of the following respective micro-filler (B32) or (B33) was used instead of the micro-filler (B31):

(B32): Terafine (apparent density=0.71 g/cm³; particle size=10 μm to 30 μm), and (B33): Aerosyl 200 (apparent density=2.2 g/cm³; particle size=0.01 μm)

Example 37

Sodium acrylate (77 g), acrylic acid (22.75 g), N,N'-methylene bis-acrylamide (0.25 g) and deionized water (293 g) were put in a reaction container (1 liter) made of glass and 3 g of (B31) was added while stirring. The temperature of the mixture was maintained at 3° C.

Nitrogen gas was purged in the mixture in order to decrease the amount of dissolved oxygen to 1 ppm or less. Afterwards, an aqueous solution of hydrogen peroxide (1%, 1 g), an aqueous solution of ascorbic acid (0.2%, 1.2 g), and an aqueous solution of 2,2'-azo-bis-amidinopropane dihydrochloride (2%, 2.8 g) were added and mixed to initiate a polymerization reaction. After five hours of polymerization, a hydrogel polymer mixture (AB1) containing a built-in (B31) was obtained.

After cutting the hydrogel polymer mixture (AB1) to a size of 2 mm to 5 mm using an internal mixer, the mixture was dried using a through-flow band dryer (150° C., air flow speed of 2.0 m/sec.). The resulting dried substance was ground so as to adjust the particle size to 20 to 100 mesh. Afterwards, 10% ethylene glycol diglycidyl ether in a water/methanol mixed solution (water/methanol=70/30) (2 g) was added to 100 g of the ground dried substance being stirred at high speed. The composition was subjected to a thermal crosslinking process (140° C., 30 min.) to obtain an absorbent composition (37).

Example 38

The hydrogel polymer (A3G) was obtained by using the same procedure as in Example 8. After (B31) of the same amount as in Example 31 was added to the hydrogel polymer (A3G) and mixed homogeneously, the mixture was dried by using a through-flow band dryer (150° C., air flow speed of 2.0 m/sec.). The resulting dried substance was ground so as to adjust the particle size to 20 to 100 mesh to obtain a water absorbent. Then, 10% ethylene glycol diglycidyl ether in a water/methanol mixed solution (water/methanol=70/30) (2 g) was added to 100 g of this water absorbent being stirred at high speed. The composition was subjected to a thermal crosslinking process (140° C., 30 min.) to obtain an absorbent composition (38).

Comparative Example 20

After 3 g of (B31) and 295 g of deionized water were added to the water absorptive resin (A1) obtained in Example 1 and mixed homogeneously by using an internal mixer, the mixture was dried by using a through-flow band dryer (150° C., air flow speed of 2.0 m/sec.). The resulting dried substance was ground so as to adjust the particle size to 20 to 100 mesh to obtain a comparative absorbent composition (c20). The specific surface area of the comparative absorbent composition (c20) was measured and an increasing rate of the specific surface area was calculated. Results are shown in Table 7. Also, results of the evaluation on the performance of the comparative absorbent composition (20) are shown in Table 8.

The increasing rate of the specific surface area of the following comparative absorbent compositions 21 to 24, respectively, was calculated in the same manner and results are shown in Table 7. Also, results of the evaluation on the performance of the comparative absorbent compositions 21 to 24 are shown in Table 8.

Comparative Example 21

After cutting the hydrogel polymer (A1G) obtained in Example 1 to a size of 2 to 5 mm using an internal mixer, 0.1 g of ethylene glycol diglycidyl ether was added. Then the mixture was mixed homogeneously by using an internal mixer and dried by using a through-flow band dryer (150° C., air flow speed of 2.0 m/sec.). The resulting dried substance was ground so as to adjust the particle size to 20 to 100 mesh to obtain a comparative absorbent composition (c21).

Comparative Examples 22 and 23

Each of the dried substances of 30 to 60 mesh particle size were obtained by using the same procedure as in Example 32 except that the amount of (B31) added was changed to 0.01 g or 15 g, respectively. Each of the dried substances of 30 to 60 mesh particle size was subjected to a crosslinking process as in Example 32 and comparative absorbent compositions (c22) and (c23) were obtained.

Comparative Example 24

100 parts of the comparative absorbent composition (c21) obtained in Comparative Example 21 was added to a mixture and stirred for a sufficient time. The mixture was obtained by mixing 15 parts of 10% aqueous solution of polyvinyl alcohol (saponification degree of 88 mol %) with 100 parts of foaming silas ("Silax PB 10", Silax Co.; average particle size of 470 μm). After that the mixture was left to stand for one hour, it was dried (120° C., 3 hour.) to obtain a comparative absorbent composition (c24).

TABLE 7

| | Water absorptive resin | | Absorbent composition | | Increasing rate of Specific surface area |
|---|---|---|---|---|---|
| | Mark | Specific surface area S1 | Mark | Specific surface area S2 | (s2 − s1)/s1 × 100 |
| Ex.31 | (A2) | 0.42 | (31) | 0.55 | 30.9 |
| Ex.32 | (A2) | 0.42 | (32) | 0.50 | 19.0 |
| Ex.33 | (A2) | 0.42 | (33) | 0.47 | 11.9 |
| Ex.34 | (A2) | 0.42 | (34) | 0.65 | 54.8 |
| Ex.35 | (A2) | 0.42 | (35) | 0.52 | 23.8 |
| Ex.36 | (A2) | 0.42 | (36) | 0.49 | 16.7 |
| Ex.37 | (A2) | 0.42 | (37) | 0.58 | 38.1 |
| Ex.38 | (A3) | 0.43 | (38) | 0.52 | 20.9 |
| C.Ex.20 | (A1) | 0.42 | (c20) | 0.46 | 9.5 |
| C.Ex.21 | (A1) | 0.42 | (c8) | 0.44 | 4.8 |
| C.Ex.22 | (A2) | 0.42 | (c21) | 0.43 | 2.4 |
| C.Ex.23 | (A2) | 0.42 | (c22) | 1.06 | 152.3 |
| C.Ex.24 | (A2) | 0.42 | (c23) | 0.91 | 116.6 |

TABLE 8

| | Absorbent composition | Diffusive Absorption speed (ml/g) | Initial absorbency under load (g/g) | Absorbency under the load (g/g) | Retention (g/g) | Rapture stress (N/m$^2$) |
|---|---|---|---|---|---|---|
| Ex.31 | (1) | 35 | 22 | 29 | 35 | 30 |
| Ex.32 | (2) | 33 | 25 | 32 | 38 | 26 |
| Ex.33 | (3) | 28 | 27 | 33 | 38 | 30 |
| Ex.34 | (4) | 34 | 26 | 31 | 37 | 26 |
| Ex.35 | (5) | 32 | 25 | 30 | 38 | 30 |
| Ex.36 | (6) | 33 | 25 | 31 | 39 | 31 |
| Ex.37 | (7) | 31 | 26 | 32 | 38 | 28 |
| Ex.38 | (8) | 32 | 27 | 33 | 41 | 30 |
| C.Ex.20 | (c20) | 24 | 8 | 14 | 46 | 29 |
| C.Ex.21 | (c21) | 22 | 17 | 29 | 38 | 27 |
| C.Ex.22 | (c22) | 22 | 19 | 31 | 39 | 30 |
| C.Ex.23 | (c23) | 18 | 18 | 28 | 37 | 20 |
| C.Ex.24 | (c24) | 15 | 5 | 10 | 17 | 29 |

Examples 39 and 40

An absorbent composition (39) and an absorbent composition (40) were obtained by adding polyoxyethylene denatured silicone oil to the absorbent compositions 32 and 33, respectively, by using the same procedure as in Example 17. Results of the evaluation on the performance of the absorbent compositions 39 and 40 are shown in Table 9.

Example 41

An absorbent composition (41) was obtained by adding polyoxyethylenenonylphenyl ether to the absorbent composition (34) by using the same procedure as in Example 26. Results of the evaluation on the performance of the absorbent composition 41 are shown in Table 9.

TABLE 9

Bulk Density of Absorbent Compositions and
Results of Evaluation of Absorbent Compositions using Sheep Blood

| Examples | Absorbent composition | Bulk density (g/cm$^3$) | Absorption speed for sheep blood (sec) | Retention after swelling in sheep blood for 30 min. (g/g) | Absorption for sheep blood under load (g/g) |
|---|---|---|---|---|---|
| 39 | (39) | 0.46 | 25 | 30 | 27 |
| 40 | (40) | 0.43 | 12 | 28 | 26 |
| 41 | (41) | 0.52 | 19 | 39 | 28 |

Examples 42 to 52

Model napkins were made using the absorbent compositions (17) to (20) obtained in Examples 17 to 20, the absorbent composition (23) obtained in Example 23, the absorbent composition (25) obtained in Example 25, the absorbent composition (29) obtained in Example 29 the absorbent composition (34) obtained in Example 34, the absorbent composition (38) obtained in Example 38, the absorbent composition (39) obtained in Example 39, and the absorbent composition (41) obtained in Example 41. Results of the evaluation on the performance of these napkins are shown in Table 10.

Comparative Examples 25 to 30

Comparative model napkins were made by using the comparative absorbent composition (c9) obtained in Comparative Example 9, the comparative absorbent composition (c11) obtained in Comparative Example 11, the comparative absorbent composition (c15) obtained in Comparative Example 15, and the comparative absorbent compositions (c17) to (c19) obtained in Comparative Examples 17 to 19. Results of the evaluation on the performance of these are shown in Table 10.

TABLE 10

Results of the Evaluation of the Model Napkins

| Absorbent used | Absorption speed (sec.) | Retention (g) | Diffusion Area (cm²) | Surface Dryness |
|---|---|---|---|---|
| Ex.42 | (17) | 38 | 15 | 37 | ○ |
| Ex.43 | (18) | 19 | 15 | 44 | ⊙ |
| Ex.44 | (19) | 24 | 16 | 41 | ○~⊙ |
| Ex.45 | (20) | 18 | 16 | 45 | ⊙ |
| Ex.46 | (23) | 23 | 15 | 42 | ○~⊙ |
| Ex.47 | (25) | 20 | 15 | 44 | ⊙ |
| Ex.48 | (29) | 18 | 17 | 45 | ⊙ |
| Ex.49 | (34) | 22 | 15 | 43 | ⊙ |
| Ex.50 | (38) | 20 | 17 | 45 | ⊙ |
| Ex.51 | (39) | 18 | 16 | 43 | ○~⊙ |
| Ex.52 | (41) | 21 | 17 | 42 | ○~⊙ |
| C. Ex.25 | (c9) | 66 | 8 | 26 | X |
| C. Ex.26 | (c11) | 60 | 9 | 29 | X |
| C. Ex.27 | (c15) | 53 | 12 | 35 | X~Δ |
| C. Ex.28 | (c17) | 58 | 10 | 28 | X |
| C. Ex.29 | (c18) | 49 | 12 | 36 | Δ |
| C. Ex.30 | (c19) | 57 | 10 | 30 | X |

While only several embodiments have been chosen to illustrate the present invention, it will be apparent to those skilled in the art from this disclosure that various changes and modifications can be made herein without departing from the scope of the invention as defined in the appended claims. Furthermore, the foregoing description of the embodiments according to the present invention are provided for illustration only, and not for the purpose of limiting the invention as defined by the appended claims and their equivalents.

What is claimed is:

1. An absorbent composition produced by a method comprising drying a mixture obtained by mixing a micro-filler (B) with a hydrogel having a water absorptive resin (A) and water;
   said hydrogel being produced by performing polymerization without drying said hydrogel between said polymerization of said hydrogel and said mixing of micro-filler (B) with said hydrogel;
   said absorbent composition having a specific surface area at least 10% larger than that of a reference composition produced by mixing said micro-filler (B) with a dried gel, said dried gel of said reference composition being produced by obtaining said hydrogel by performing said polymerization and drying said hydrogel between said polymerization of said hydrogel and said mixing of micro-filler (B) with said hydrogel.

2. An absorbent composition according to claim 1, wherein said absorbent composition has an absorption speed (a time required for absorbing a certain amount) for physiological saline at least 20% less than that of said reference composition.

3. An absorbent composition according to claim 1, wherein
   said absorbent composition is a particle type absorbent having an average diameter that is in the range of 200 μm to 600 μm;
   said absorbent has particles of which diameters are between 150 μm and 500 μm; and specific surface areas are at least 0.1 m²/g by BET method.

4. An absorbent composition according to claim 1, wherein
   said absorbent composition has an absorption speed (a time required for absorbing a certain amount) for physiological saline at 25 seconds or less.

5. An absorbent composition according to claim 1, wherein
   said absorbent composition has a mass ratio of said water absorptive resin (A) and said micro-filler (B) in the range of 100:005 and 100:10.

6. An absorbent composition according to claim 1, wherein
   said absorbent composition has an apparent density of said micro-filler (B) that is 0.5 g/cm³ or less.

7. An absorbent composition according to claim 1, wherein
   said micro-filler (B) has an apparent density of 0.1 g/cm³ or less and an average particle size in the range of 1 μm to 200 μm.

8. An absorbent composition according to claim 7, wherein
   said micro-filler (B) has hollowed particles made of at least one selected from the group consisting of polyacrylate, polymethacrylate, polyvinylidene chloride, polyvinyl acetate and polyacrylonitrile.

9. An absorbent composition according to claim 1, wherein
   said micro-filler (B) is obtained by thermally expanding a thermal expansile hollowed filler having an average particle size in the range of 1 μm to 150 μm.

10. An absorbent composition according to claim 9, wherein said micro filler (B) is a hollowed resin filler containing a gas or a volatile substance inside thereof.

11. An absorbent composition according to claim 9, wherein
    said micro-filler (B) has a volume at least ten times as much as said thermal expansile hollowed filler.

12. An absorbent composition according to claim 1, wherein
    said micro-filler (B) has an apparent density which is more than 0.1 g/cm³ and not more than 5 g/cm³ and an average particle size in the range of 0.001 to 200 μm.

13. An absorbent composition according to claim 12, wherein
    said micro-filler is an inorganic filler.

14. An absorbent composition according to claim 12, wherein
    said micro-filler is made of one or a mixture of at least two selected from the group consisting of silicon oxide, aluminum oxide, iron oxide, titanium oxide, magnesium oxide, and zirconium oxide.

15. An absorbent composition according to claim 1, wherein said method further comprising:

adding a surface active agent (C) to said mixture after said drying.

16. An absorbent composition according to claim 15, wherein said surface active agent (C) is a nonionic surface active agent having an HLB of 8 to 14.

17. An absorbent composition comprising surface crosslinking particles containing a built-in micro-filler (B) obtained by a method comprising:

obtaining particles by drying and grinding a mixture obtained by mixing said micro-filler (B) with a hydrogel having a water absorptive resin (A) and water, said hydrogel being produced by performing polymerization without drying said hydrogel between said polymerization of said hydrogel and said mixing of microfiller (B) with said hydrogel; and surface-crosslinking a surface and a proximity of said surface of each of said particles by using a crosslinking agent;

said absorbent composition having a specific surface area at least 10% larger than that of a reference composition produced by mixing said micro-filler (B) with a dried gel, said dried gel of said reference composition being produced by obtaining said hydrogel by performing said polymerization and drying said hydrogel between said polymerization of said hydrogel and said mixing of micro-filler (B) with said hydrogel.

18. An absorbent composition according to claim 17, wherein said mixture contains said water 2 to 10 times as much as said water absorptive resin (A).

19. An absorbent composition according to claim 17, wherein said resin (A) has a crosslinked structure, and has an absorption amount for physiological saline under applied pressure of 20 g/cm$^2$ that is 25 g/g or more.

20. An absorbent composition according to claim 17, wherein said absorbent has a diffusive absorption speed for 0.9 mass% physiological saline in the range of 25 to 65 ml/g and an initial amount of absorption under applied pressure for 0.9 mass % physiological saline in the range of 18 to 40 g/g.

21. An absorbent composition produced by a method comprising adding a surface active agent (C) to a surface of adsorptive particles whose main composition is a water absorptive resin (A) having a bulk density in the range of 0.1 to 0.55 g/cm3 and an average particle size in the range of 200 to 600 $\mu$m, said absorbent composition having an absorption speed for sheep blood that is 30 seconds or faster and a water retention amount after swelling in sheep blood for 30 minutes that is 20 g/g or more.

22. A method for producing an absorbent composition comprising:

obtaining a mixture by mixing a micro-filler (B) having an apparent density of 5 g/cm$^3$ or less with a hydrogel having a water absorptive resin (A) and water, said hydrogel being produced by performing polymerization without drying said hydrogel between said polymerization of said hydrogel and said mixing of microfiller (B) with said hydrogel; and drying said mixture.

23. A method according to claim 22, wherein said micro-filler (B) has an apparent density of 0.1 g/cm$^3$ or less and an average particle size in the range of 1 $\mu$m to 200 $\mu$m.

24. A method according to claim 22, wherein said micro-filler (B) has an apparent density which is more than 0.1 g/cm$^3$ and not more than 5 g/cm$^3$ and an average particle size in the range of 0.001 $\mu$m to 200 $\mu$m.

25. A method according to claim 22, wherein said micro-filler (B) is obtained by thermally expanding a thermal expansile hollowed filler having an average particle size in the range of 1 $\mu$m to 150 $\mu$m.

26. A method according to claim 22, further comprising surface-crosslinking said mixture after said drying.

27. A method according to claim 22, further comprising adding a surface active agent (C) onto said mixture after said drying.

28. An absorbent product comprising: an absorption layer having an absorbent composition and a fibrous material, said absorbent composition produced by a method comprising drying a mixture obtained by mixing a micro-filler (B) with a gydrogel having a water absorptive resin (A) and water; said hydrogel being produced by performing polymerization without drying said hysrogel betweeen said polymerization of said hydrogel and said mixing of micro-filler (B) with said hydrogel; said absorbent composition having a specific surface area at least 10% larger tan that of a reference produced by mixing said micro-filler (B) with a dried gel. said dried gel o f said referejce composition being produced by obtaining said hydrogel by performing said polymerization and drying said hydrogel between said plymerization of said hydrogel and said mixing of micro-filler (B) with said hydrogels; adn a surface sheet covering said absorption layer, and having a water permeable portion.

* * * * *

UNITED STATES PATENT AND TRADEMARK OFFICE
CERTIFICATE OF CORRECTION

PATENT NO.     : 6,284,362 B1                                      Page 1 of 1
DATED          : October 29, 2001
INVENTOR(S)    : Hitoshi Takai et al.

It is certified that error appears in the above-identified patent and that said Letters Patent is hereby corrected as shown below:

<u>Title page,</u>
Please insert the following:

-- Related U.S. Application Data
[63]    Continuation-in-part of application No. PCT/JP98/03231, Jul. 17, 1998 --

<u>Column 1,</u>
Line 5, prior to the section entitled, BACKGROUND OF THE INVENTION, please insert the following:

-- This application is a continuation-in-part of International Application Serial No. PCT/JP98/03231, filed July 17, 1998 in Japanese. --

Signed and Sealed this

First Day of April, 2003

JAMES E. ROGAN
*Director of the United States Patent and Trademark Office*